US009994636B2

(12) United States Patent
Elvin et al.

(10) Patent No.: US 9,994,636 B2
(45) Date of Patent: Jun. 12, 2018

(54) ANTI-SIGLEC-15 ANTIBODIES AND USES THEREOF

(71) Applicants: MEDIMMUNE LIMITED, Cambridge (GB); CAMBRIDGE ENTERPRISE LIMITED, Cambridge (GB)

(72) Inventors: John Elvin, Cambridge (GB); Catherine Huntington, Cambridge (GB); John Trowsdale, Cambridge (GB); Alexander Barrow, St. Louis, MI (US); Huan Cao, Aberdeen (GB)

(73) Assignees: MedImmune Limited, Granta Park, Cambridge (GB); Cambridge Enterprise Limited, Cambridge (GB)

( * ) Notice: Subject to any disclaimer, the term of this patent is extended or adjusted under 35 U.S.C. 154(b) by 0 days. days.

(21) Appl. No.: 15/232,259

(22) Filed: Aug. 9, 2016

(65) Prior Publication Data
US 2017/0029503 A1 Feb. 2, 2017

Related U.S. Application Data

(62) Division of application No. 14/342,067, filed as application No. PCT/EP2012/067454 on Sep. 6, 2012, now Pat. No. 9,447,192.

(60) Provisional application No. 61/532,658, filed on Sep. 9, 2011.

(51) Int. Cl.
| C07K 16/00 | (2006.01) |
| C07K 16/28 | (2006.01) |
| C07K 16/30 | (2006.01) |

(52) U.S. Cl.
CPC .......... C07K 16/2803 (2013.01); C07K 16/30 (2013.01); *C07K 2317/33* (2013.01); *C07K 2317/56* (2013.01); *C07K 2317/565* (2013.01); *C07K 2317/77* (2013.01)

(58) Field of Classification Search
None
See application file for complete search history.

(56) References Cited

U.S. PATENT DOCUMENTS

| 9,447,192 B2 * | 9/2016 | Elvin ................. C07K 16/2803 |
| 2002/0110862 A1 | 8/2002 | Foussias et al. |
| 2010/0209428 A1 | 8/2010 | Hiruma et al. |
| 2011/0268733 A1 | 11/2011 | Hiruma et al. |

FOREIGN PATENT DOCUMENTS

| WO | WO2007/049044 | 3/2007 |
| WO | WO 2009/048072 A1 | 4/2009 |
| WO | WO 2010/117011 A1 | 10/2010 |
| WO | WO 2011/041894 A1 | 4/2011 |

OTHER PUBLICATIONS

Angata, T, et al., "Discovery of Siglec-14, a novel sialic acid receptor undergoing concerted evolution with Siglec-5 in primates," The FASEB Journal, vol. 20, No. 12, pp. 1964-1973 (Oct. 2006).
Angata, T., et al., "Siglec-15: An immune system Siglec conserved throughout vertebrate evolution," Glycobiology, vol. 17, Issue 8, pp. 838-846 (Aug. 2007).
Bhatia, M., et al., "Purification of primitive human hematopoietic cells capable of repopulating immune-deficient mice," Proceedings of the National Academy of Sciences, vol. 94, Issue 10, pp. 5320-5325 (May 1997).
Bross, P. F., et al., "Approval Summary: Gemtuzumab Ozogamicin in Relapsed Acute Myeloid Leukemia," Clinical Cancer Research, vol. 7, Issue 6, pp. 1490-1496 (Jun. 2001).
Brown, M., et al., "Tolerance of single, but not multiple, amino acid replacements in antibody VH CDR 2: a means of minimizing B cell wastage from somatic hypermutation?", Journal of Immunology, vol. 156(9), pp. 3285-3291 (May 1996).
Burnett, A. K., et al., "Identification of patients with acute myeloblastic leukemia who benefit from the addition of gemtuzumab ozogamicin: results of the MRC AML15 trial," Journal of Clinical Oncology, vol. 29, Issue 4, pp. 369-377 (Feb. 1, 2011).
Cao, H., et al., "SIGLEC16 encodes a DAP12-associated receptor expressed in macrophages that evolved from its inhibitory counterpart SIGLEC11 and has functional and non-functional alleles in humans," European Journal of Immunology, vol. 38, Issue 8, pp. 2303-2315 (Aug. 2008).
Casset, F., et al., "A peptide mimetic of an anti-CD4 monoclonal antibody by rational design", BBRC, vol. 307(1), pp. 198-205, (Jul. 2003).
Chan, W. I., and Huntly, B. J. P., "Leukemia Stem Cells in Acute Myeloid Leukemia," Seminars in Oncology, vol. 35, Issue 4, pp. 326-335 (Aug. 2008).
Faure, M., and Long, E. O., "KIR2DL4 (CD158d), an NK cell-activating receptor with inhibitory potential," The Journal of Immunology, vol. 168, Issue 12, pp. 6208-6214 (Jun. 15, 2002).
George, J., et al., "Differential Effects of Anti-β2-Glycoprotein I Antibodies on Endothelial Cells and on the Manifestations of Experimental Antiphospholipid Syndrome", Circulation, vol. 97(9), pp. 900-906 (Mar. 1998).
Hiruma, Y., et al., "Siglec-15, a member of the sialic acid-binding lectin, is a novel regulator for osteoclast differentiation," Biochemical and Biophysical Research Communications, vol. 409, No. 3, pp. 424-429 (Jun. 2011).
International Preliminary Report on Patentability in International Application No. PCT/EP2012/067454, dated Mar. 12, 2014.
International Search Report for International Application No. PCT/EP2012/067454, dated Feb. 7, 2013.
Written Opinion for International Application No. PCT/EP2012/067454, dated Feb. 7, 2013.
Kikuchi-Maki, A., et al., "Cutting Edge: KIR2DL4 Transduces Signals into Human NK Cells through Association with the Fc Receptor γ Protein," The Journal of Immunology, vol. 174, No. 7, pp. 3859-3863 (Apr. 1, 2005).

(Continued)

*Primary Examiner* — Sheela J. Huff

(57) ABSTRACT

This disclosure relates to anti-Siglec-15 antibodies and uses thereof, in particular in the treatment of leukaemia, such as acute myeloid leukaemia.

11 Claims, 12 Drawing Sheets

(56) References Cited

OTHER PUBLICATIONS

Figure 1:
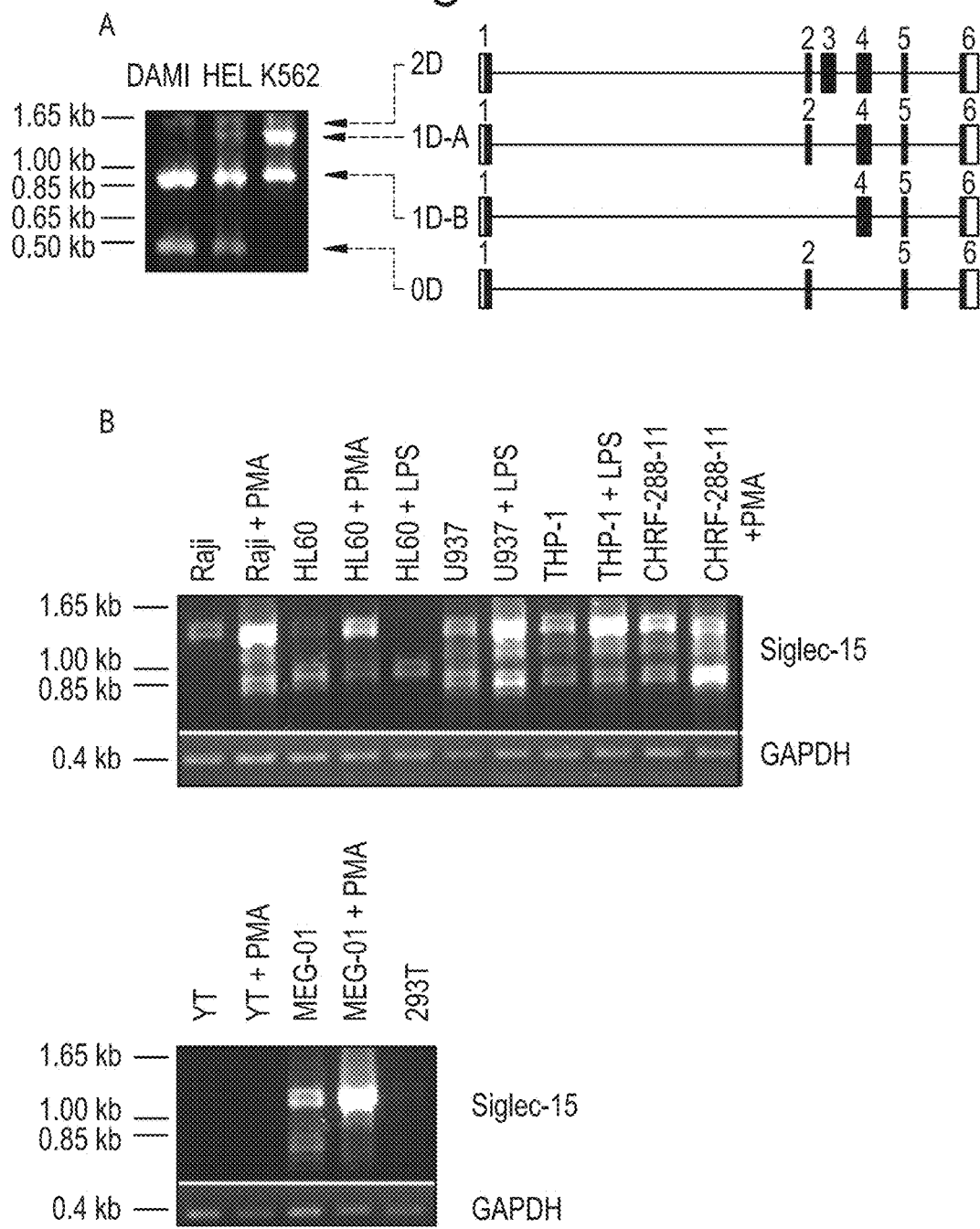

Miah, S. M. S., et al., "KIR2DL4 Differentially Signals Downstream Functions in Human NK Cells through Distinct Structural Modules," The Journal of Immunology, vol. 180, No. 5, pp. 2922-2932 (Mar. 1, 2008).

Mulford, D., "Antibody Therapy for Acute Myeloid Leukemia," Seminars in Hematology, vol. 45, Issue 2, pp. 104-109 (Apr. 2008).

Nguyen, D.H., "Myeloid precursors and acute myeloid leukemia cells express multiple CD33-related Siglecs," Experimental Hematology, vol. 34, Issue 6, pp. 728-735 (Jun. 2006).

O'Reilly, M. K. and Paulson J. C., "Siglecs as targets for therapy in immune-cell-mediated disease," Trends in Pharmacological Sciences, vol. 30, No. 5, pp. 240-248 (May 1, 2009).

Pascalis, R., et al., "Grafting of "abbreviated" complementarity-determining regions containing specificity-determining residues essential for ligand contact to engineer a less immunogenic humanized monoclonal antibody", Journal of Immunology, vol. 169(6), pp. 3076-3084, (Sep. 2002).

Paul, W.E., "Structure and Function of Immunoglobulins", Fundamental Immunology, 3$^{rd}$ Edition, pp. 292-295, (1993).

Rudikoff, S., et al., "Single amino acid substitution altering antigen-binding specificity", Proceedings of the National Academy of Sciences, vol. 79(6), pp. 1979-1983, (Mar. 1982).

Shlapatska, L. M., et al., "CD150 Association with Either the SH2-Containing Inositol Phosphatase or the SH2-Containing Protein Tyrosine Phosphatase Is Regulated by the Adaptor Protein SH2D1A," The Journal of Immunology, vol. 166, No. 9, pp. 5480-5487 (May 1, 2001).

Taussig, D. C., et al., "Anti-CD38 antibody-mediated clearance of human repopulating cells masks the heterogeneity of leukemia-initiating cells," Blood, vol. 112, Issue 3, pp. 568-575 (Aug. 2008).

Taussig, D. C., et al., "Hematopoietic stem cells express multiple myeloid markers: implications for the origin and targeted therapy of acute myeloid leukemia," Blood, vol. 106, Issue 13, pp. 4086-4092 (Dec. 2005).

Vajdos, F. F., et al., "Comprehensive functional maps of the antigen-binding site of an anti-ErbB2 antibody obtained with shotgun scanning mutagenesis", Journal of Molecular Biology, vol. 320(2), pp. 415-428 (Jul. 2002).

Varki, A., and Angata, T., "Siglecs—the major subfamily of I-type lectins," Glycobiology, vol. 16, No. 1, pp. 1R-27R (Jan. 2006).

\* cited by examiner

Figure 2
A. FACS
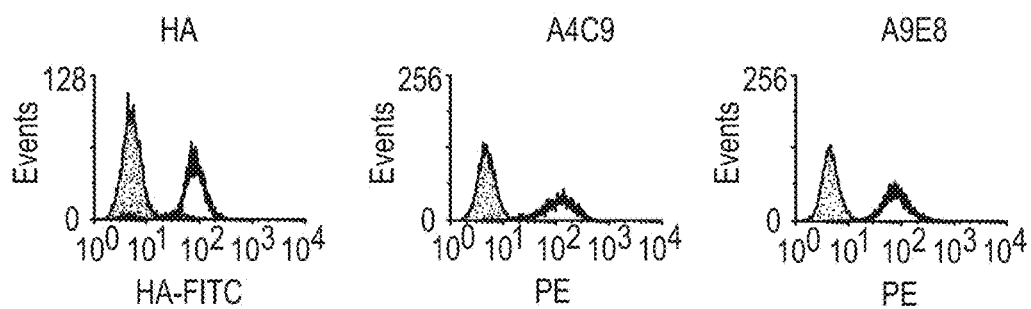
B. Confocal
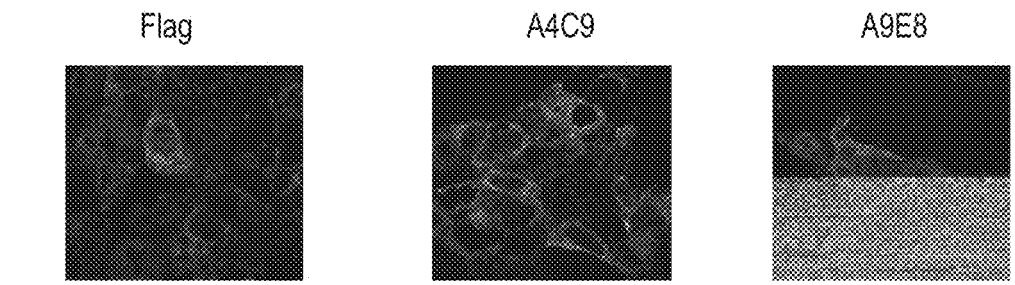
C. FMAT -specificity
D. Western - A4C9
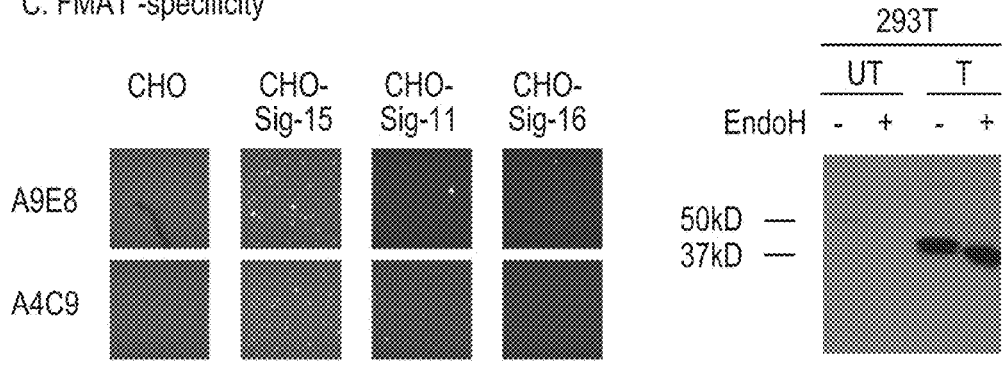

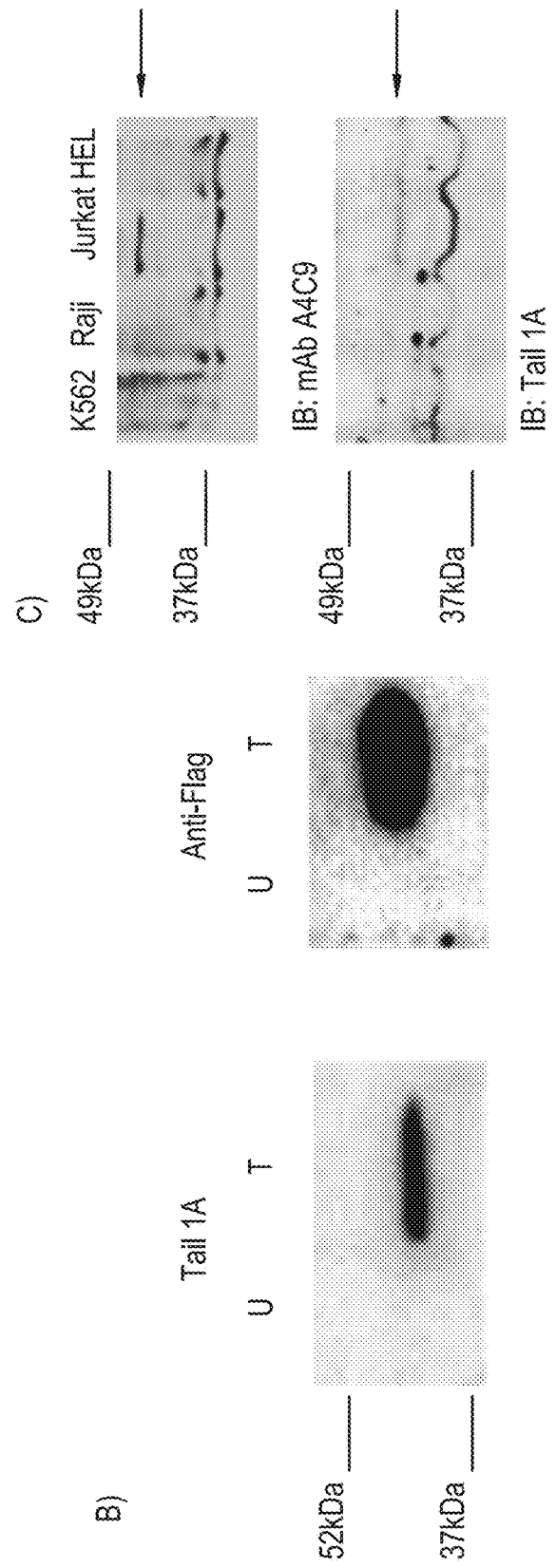

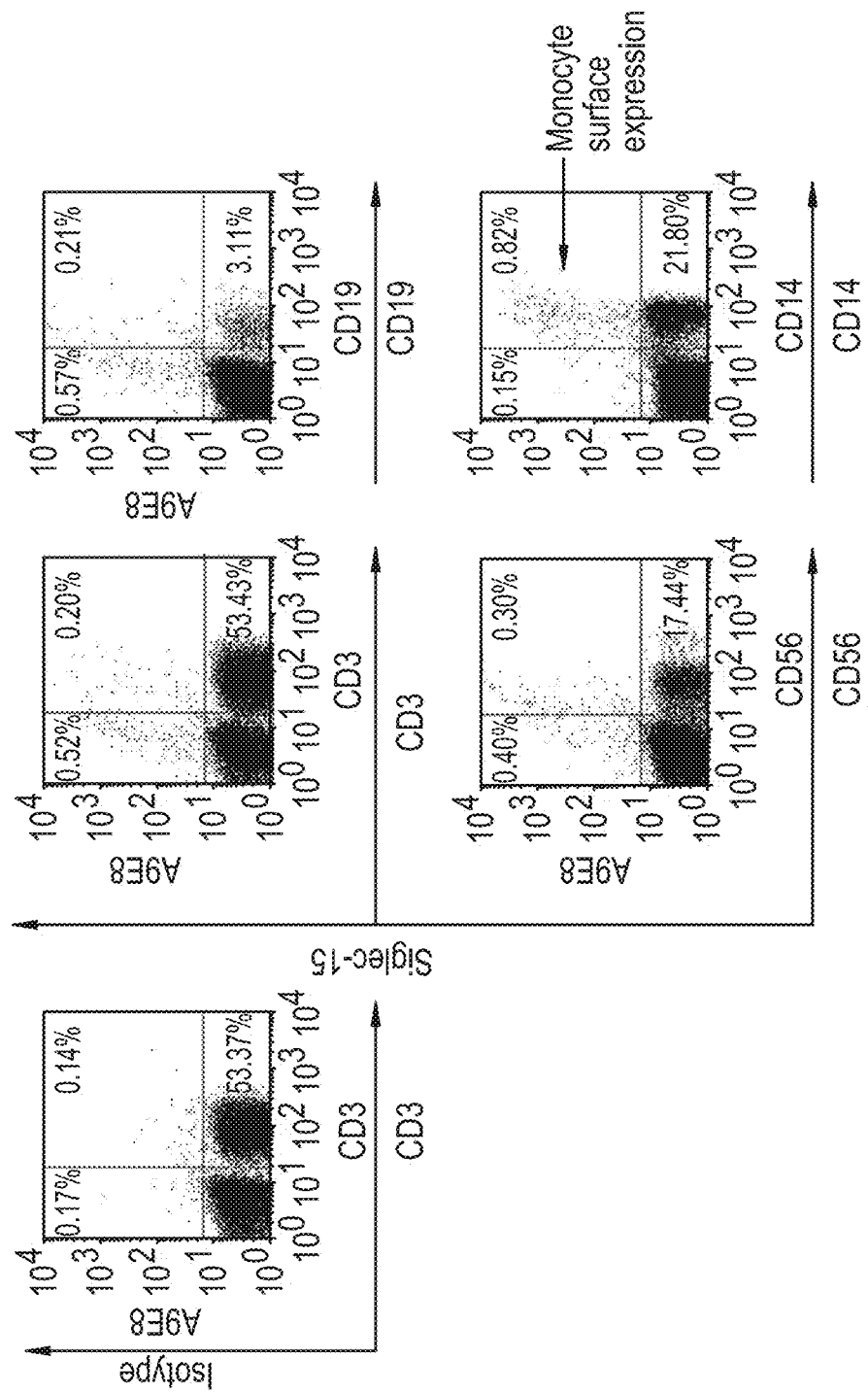

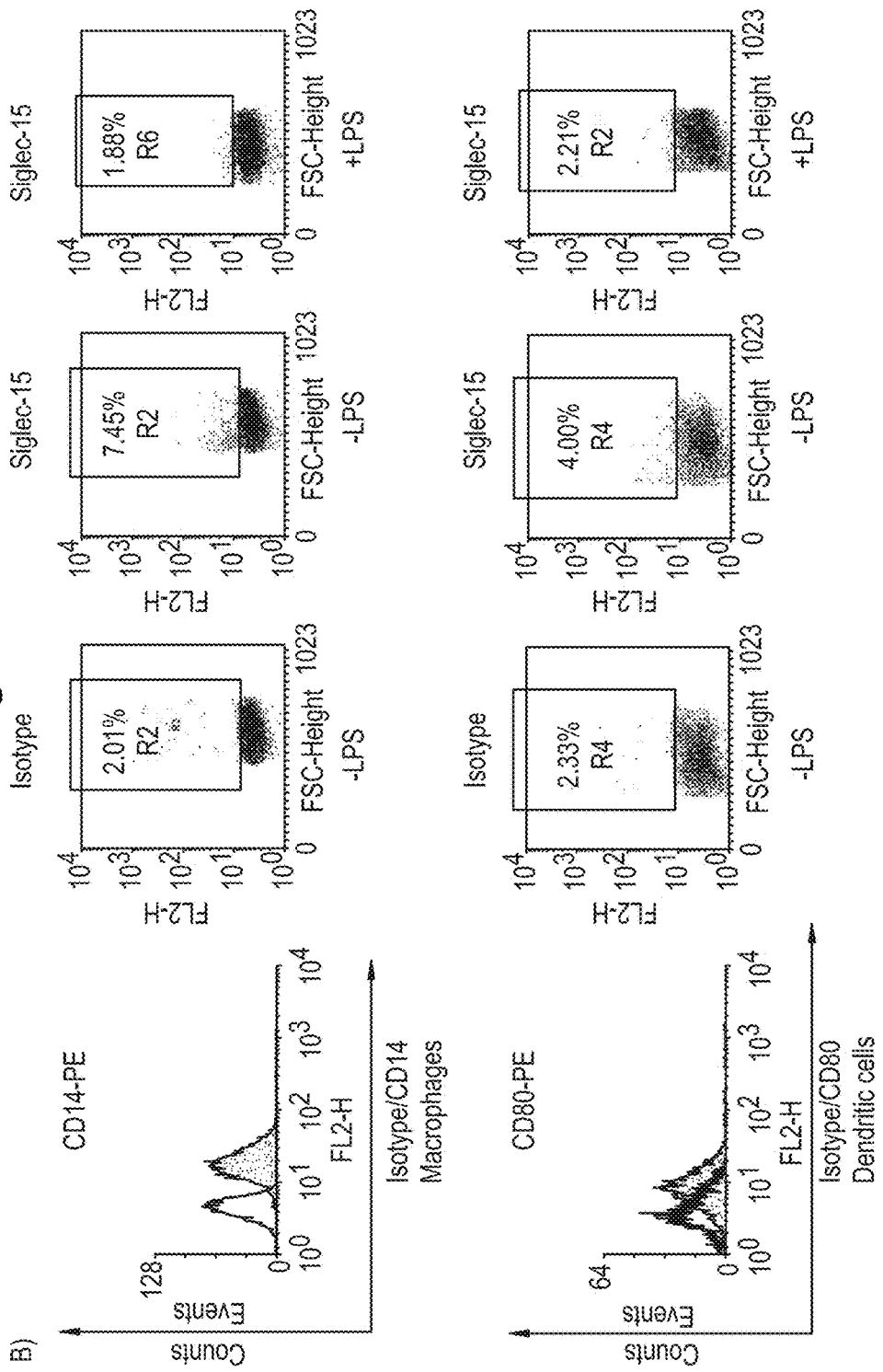

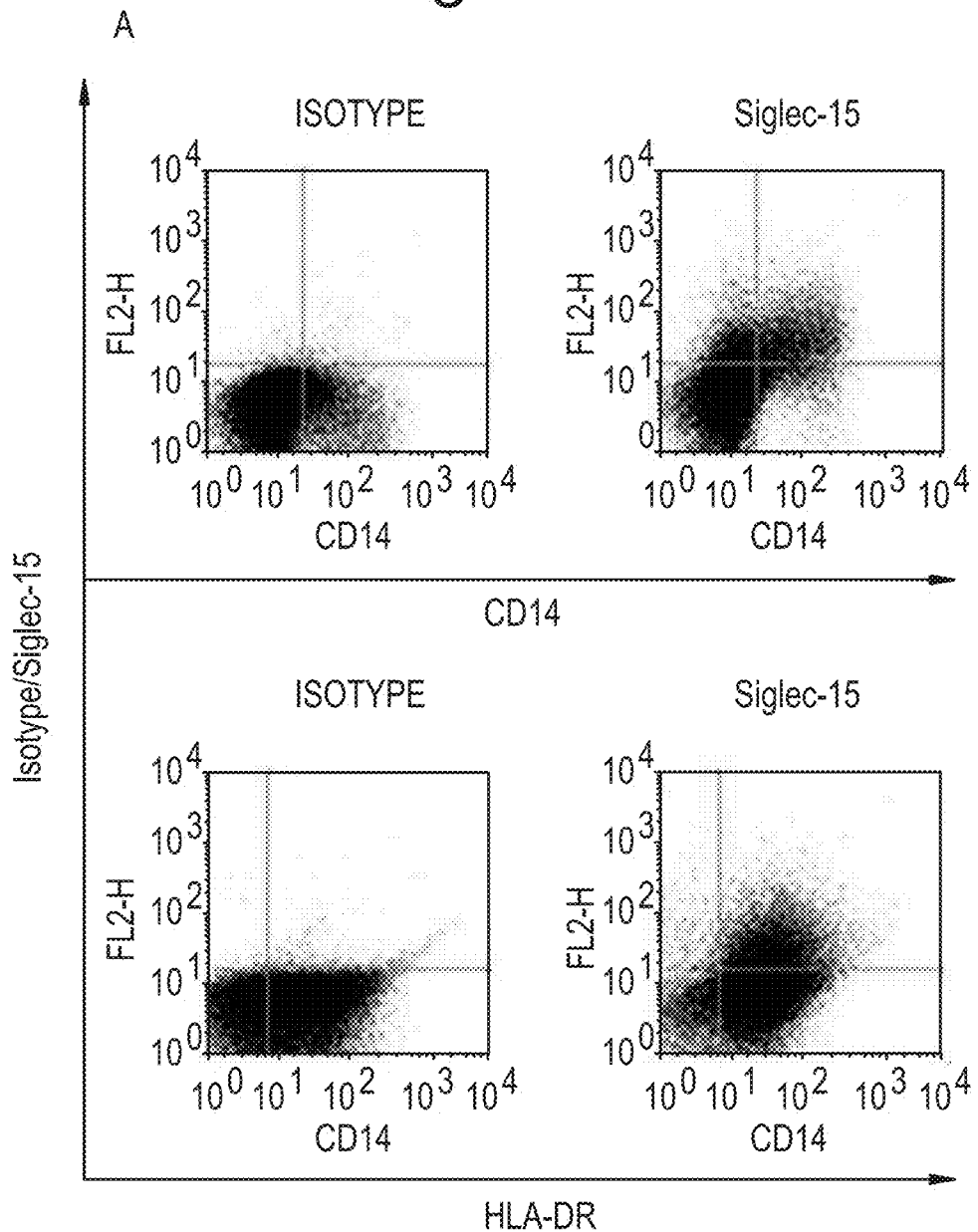

Figure 8
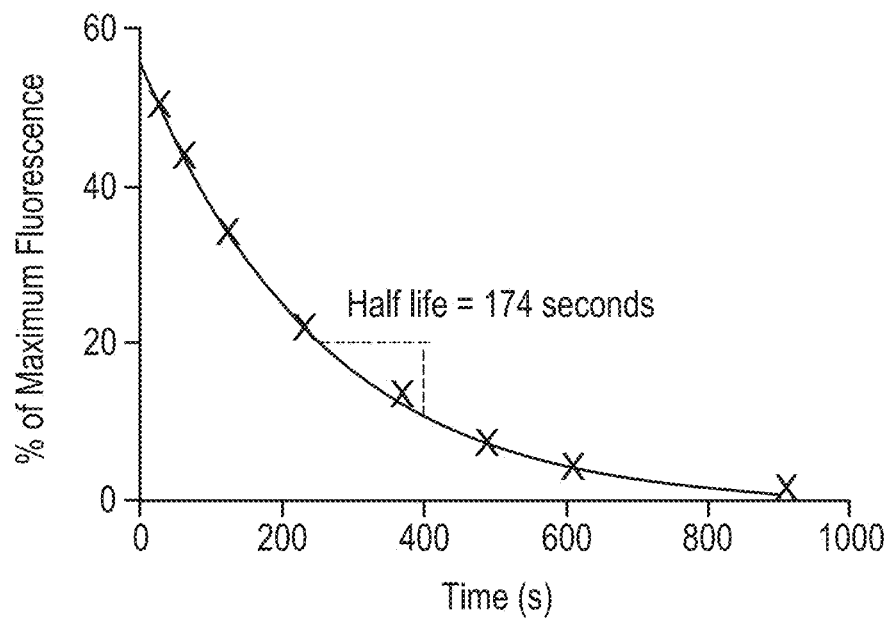
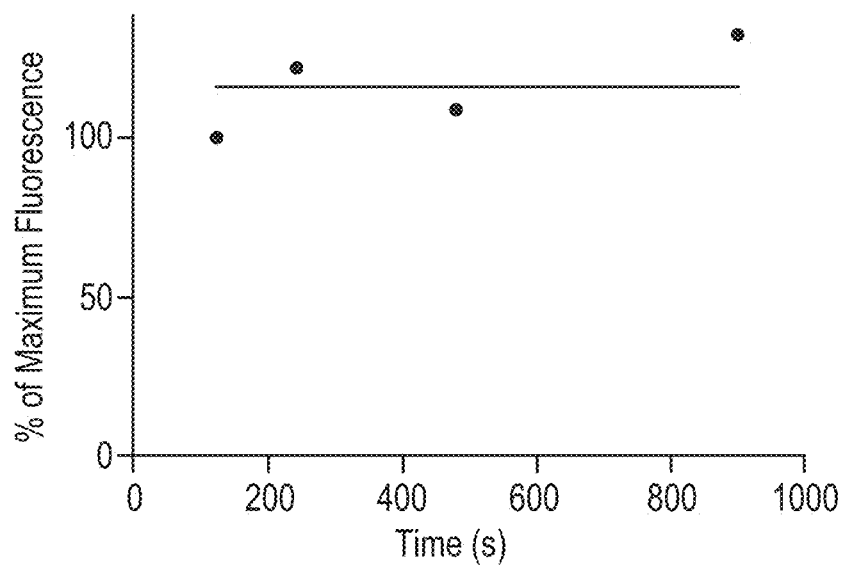

SEQUENCE LISTING

```
<160> NUMBER OF SEQ ID NOS: 11

<210> SEQ ID NO 1
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Gln Leu Gln Leu Gln Glu Ser Gly Pro Gly Leu Val Lys Pro Ser Glu
1               5                   10                  15

Thr Leu Ser Leu Thr Cys Ala Val Ser Gly Ala Ser Ile Ser Asn Trp
            20                  25                  30

Trp Ser Trp Val Arg Gln Pro Pro Gly Lys Gly Leu Glu Trp Ile Gly
        35                  40                  45

Glu Val His His Ser Gly Val Thr Thr Tyr Lys Pro Ser Leu Lys Ser
    50                  55                  60

Arg Val Thr Ile Ser Val Asp Asn Ser Lys Asn Gln Leu Ser Leu Lys
65                  70                  75                  80

Leu Thr Ser Val Thr Ala Ala Asp Thr Ala Val Tyr Tyr Cys Ala Arg
                85                  90                  95

Glu Phe Ala Asp Asp Ala Phe Asp Ile Trp Gly Arg Gly Thr Met Val
            100                 105                 110

Thr Val Ser Ser
        115

<210> SEQ ID NO 2
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Ser Ser Glu Leu Thr Gln Asp Pro Ala Val Ser Val Ala Leu Gly Gln
1               5                   10                  15

Thr Val Arg Ile Thr Cys Arg Gly Asp Ser Leu Arg Lys Tyr Tyr Ala
            20                  25                  30

Ser Trp Tyr Gln Gln Lys Pro Arg Gln Ala Pro Gln Leu Val Ile Tyr
        35                  40                  45

His Lys Asn Asn Arg Ala Ser Gly Ile Pro Asp Arg Phe Ser Gly Ser
    50                  55                  60

Ile Ser Gly Asn Thr Ala Ser Leu Thr Ile Thr Gly Ala Gln Ala Glu
65                  70                  75                  80

Asp Glu Ala Ala Tyr Phe Cys Asn Ser Arg Asp Thr Ser Gly Asn Tyr
                85                  90                  95

Leu Val Phe Gly Gly Gly Thr Lys Val Thr Val Leu Gly
            100                 105
```

```
<210> SEQ ID NO 3
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Asn Trp Trp Ser
1

<210> SEQ ID NO 4
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Glu Val His His Ser Gly Val Thr Thr Tyr Lys Pro Ser Leu Lys Ser
1               5                   10                  15

<210> SEQ ID NO 5
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Glu Phe Ala Asp Asp Ala Phe Asp Ile
1               5

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Arg Gly Asp Ser Leu Arg Lys Tyr Tyr Ala Ser
1               5                   10

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

His Lys Asn Asn Arg Ala Ser
1               5

<210> SEQ ID NO 8
<211> LENGTH: 11
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Asn Ser Arg Asp Thr Ser Gly Asn Tyr Leu Val
1               5                   10

<210> SEQ ID NO 9
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
cagctgcagc tgcaggagtc gggcccagga ctggtgaagc cttcggaaac cctgtccctc      60
acctgcgctg tctctggtgc ctccattagt aactggtgga cttgggtccg ccagccccca     120
gggaaggggc tggagtggat tggggaagtc catcatagtg gagtcaccac ctacaagccg     180
tccctcaaga gtcgagtcac catatcagta gacaactcga agaaccaatt atctctgaag     240
ctaacctctg tgacagccgc ggacacggcc gtgtattact gtgcgagaga gttcgcggat     300
gatgcttttg atatctgggg ccagggaca atggtcaccg tctcgagt                   348

<210> SEQ ID NO 10
<211> LENGTH: 326
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
tcttctgagc tgactcagga ccctgctgtg tctgtggcct gggacagaca gtcaggatca      60
catgccgagg ggacagcctc agaaagtatt atgcaagctg gtaccagcag aagccacgac     120
aggcccctca acttgtcatc tatcataaaa acaacagggc gtcagggatc ccagaccgat     180
tctctggctc catctccgga aacacagctt ctttgaccat cactggggct caggcagaag     240
atgaggctgc ctatttctgt aattctcggg acaccagtgg taattatctg gtcttcggcg     300
gagggaccaa ggtcaccgtc ctaggt                                          326

<210> SEQ ID NO 11
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ser Asn Tyr Glu Asn Leu
1               5
```

ANTI-SIGLEC-15 ANTIBODIES AND USES THEREOF

CROSS-REFERENCE TO RELATED APPLICATIONS

This application is a Divisional of U.S. application Ser. No. 14/342,067, filed Oct. 10, 2014, said U.S. application Ser. No. 14/342,067 is a U.S. National Stage application of International Application No. PCT/EP2012/067454, filed on Sep. 6, 2012, said International Application No. PCT/EP2012/067454 claims benefit under 35 U.S.C. §119(e) of the U.S. Provisional Application No. 61/532,658, filed Sep. 9, 2011. Each of the above listed applications is incorporated by reference herein in its entirety for all purposes.

STATEMENT REGARDING FEDERALLY SPONSORED RESEARCH OR DEVELOPMENT

This invention was made in part during work supported by funding from the European Community's Seventh Framework Programme ([FP7/2007-2013] under grant agreement no RG55610.

REFERENCE TO THE SEQUENCE LISTING

This application incorporates by reference a Sequence Listing submitted with this application as text file entitled SIG15-100US1_SEQ, created on Feb. 12, 2014, and having a size of 8 kilobytes.

BACKGROUND

Field of the Disclosure

This Disclosure Relates to Anti-Siglec-15 Immunoconjugates, Antibodies, Antigen-Binding fragments and uses thereof, in particular in the treatment of acute myeloid leukaemia.

Background of the Disclosure

Acute myeloid leukaemia (AML) is a fatal illness where normal haematopoiesis is replaced with a malignant proliferation of immature blast cells. The symptoms, such as infection, bleeding, and anaemia, are related to this bone marrow failure and if left untreated will lead to the death of the patient. AML affects around 2,000 people a year in the UK, with an increasing incidence as the population ages. Curative treatment is highly intensive, which is arduous for the patient, expensive, and requires prolonged hospital admissions, presenting a significant cost to the national health system. In addition, the use of allogeneic bone marrow transplantation, either up-front or for salvage therapy, represents a further cost in those patients for whom it is appropriate. Despite this, the majority of patients with AML still die from the disease.

Many drugs have been developed to treat AML. In addition to conventional chemotherapy agents, therapeutic antibodies have been developed to selectively target AML blasts. Gemtuzumab ozogamicin (GO), targeting a sialic acid binding immunoglobulin-like Siglec protein, CD33, is approved for patients over 60 years of age (Bross P F et al., Clin. Cancer Res. 7(6):1490-6 (2001)).

CD33 is an antigen found on many AML blasts and GO is a toxin-conjugated antibody that binds CD33. Recently, a randomized trial (AML15) reported a disease-free survival advantage for patients treated with GO, mainly related to a decreased incidence of relapse (Burnett A K et al., J. Clin. Oncol. 29(4):369-77 (2011)). However, approximately 10% cases of AML do not express CD33 and GO is also associated with relatively rare, but potentially life-threatening side effects which include myelosuppression, perhaps because CD33 is expressed on healthy hematopoietic stem cells (Taussig D C et al., Blood 106(13): 4086-92 (2005)). In the AML15 trial this side effect appeared to have been manifested by the fact that patients treated with GO required more platelet transfusions and IV antibiotics. In other studies, treatment with GO has also resulted in hepatotoxicity as a dose limiting side effect (Mulford D., Semin. Hematol. 45(2):104-9 (2008)).

Although the existence of cancer stem cells for all malignancies is a much debated topic, it is widely accepted that they are present in leukaemia. The first evidence for the existence of cancer stem cells was demonstrated in acute myeloid leukaemia. Bonnet and Dick isolated the CD34+ CD38− subpopulation of leukemic cells and showed that these cells could repopulate tumors in NOD/SCID mice (Bhatia M. et al., Proc. Natl. Acad. Sci. 94(10):5320-5 (1997)). Recent work also suggested that leukaemia stem cell potential is present in the CD38+ compartment (Taussig D C et al., Blood 112(3): 568-75 (2008)). With a growing knowledge of their biology and unique identity, work is beginning to target leukemic stem cells (Chan W I and Huntly B J, Semin. Oncol. 35(4):326-35 (2008)). In leukaemia therapy, active research is targeting this leukaemic stem cell subpopulation, however no drug is available to date that targets these cells specifically.

Siglecs are a family of immunoglobulin superfamily receptors that bind sialic acids (Varki A and Angata T, Glycobiology 16(1):1R-27R (2006)). They are commonly expressed on immune cells, in particular those immune cells of the myeloid lineage. Most Siglecs are inhibitory, but novel activating Siglecs have been discovered recently, namely Siglec-14, -15 and 16 (Angata T et al., FASEB J. 20:1964-1973 (2006), Angata T et al., Glycobiology 17:838-846 (2007), Cao H et al., Eur. J. Immunol. 38:2303-2315 (2008)). Different Siglecs have varying affinities for distinct linkages of sialic acids, which are nine carbon based sugars found at the periphery of most mammalian cell surfaces. Siglec-15 is a newly described Siglec that is well conserved between species with recognizable orthologues of the human sequence in zebrafish. Initial characterisation of Siglec-15 revealed α-2,6 linked sialic acids as its ligand, binding of which was dependent on an essential arginine residue in Siglec-15's N-terminal V-set immunoglobulin domain (Angata T et al., 2007). Siglec-15 has also been shown to bind an antigen highly expressed in a variety of tumors, sialyl-Tn (Angata T et al., 2007). Siglec-15 is unusual in that it is equipped with both negative and positive signalling motifs. In the transmembrane domain, Siglec-15 can associate with positive signalling adaptor molecules, such as DAP10, DAP12 and Fc receptor common γ chain but, at the same time, Siglec-15 encodes a cytoplasmic ITIM-like motif known as immunoreceptor-tyrosine based switch motif (ITSM) that generally mediates inhibitory signals (Shlapatska L M et al., J Immunol. 166(9):5480-7 (2001)). The only other example of an immune receptor encoding dual signalling motifs is KIR2DL4, which associates with ITAM encoding adaptor Fc receptor common γ chain (Miah S M et al., J. Immunol., 180(5):2922-32 (2008)); Kikuchi-Maki A et al., J. Immunol., 174(7):3859-63 (2005)) and also contains an inhibitory ITIM motif in its own cytoplasmic tail (Faure M and Long E O, J. Immunol., 168(12):6208-14 (2002)).

Interest in Siglecs as targets for treatment of leukaemia is growing. Nguyen et al profiled the majority of the known CD33rSiglecs (a major subfamily of Siglecs) for their expression on AML cells. (Nguyen D H, *Exp. Hematol.*, 34(6):728-35 (2006)) They identified expression profiles of Siglecs characteristic of each major subgroup of AML as well as patient-specific CD33rSiglec finger prints. A customized approach to leukaemia treatment has been proposed where full profiling of a patient's Siglec expression is followed by targeting a combination of Siglecs. The advantage of targeting Siglecs is that most of them exhibit rapid endocytosis. Antibody-induced endocytosis of Siglec-5 and Siglec-9 on the surface of U937 cells have similar half-lives of approximately 100 minutes. However, no Siglec-based therapies have been developed for the treatment of AML.

BRIEF SUMMARY

The invention identifies an association between Siglec-15 expression and leukaemia. The invention also provides for Siglec-15 immunoconjugates, antibodies, and antigen-binding fragments thereof and methods of using such molecules to treat leukaemia, such as AML. Importantly, the Siglec-15 immunoconjugates, antibodies, and antigen-binding fragments provide for therapeutics that avoid the side-effects associated with CD33-targeted AML therapies.

The invention provides for an isolated antibody or antigen-binding fragment thereof that specifically binds to Siglec-15 comprising: a VH sequence at least 90%, 95% or 100% identical to the amino acid sequence of SEQ ID NO:1; a VL sequence at least 90%, 95% or 100% identical to the amino acid sequence of SEQ ID NO:2; a VH-CDR1, VH-CDR2 and/or VH CDR3 sequence identical to or identical to except for one, two, or three substitutions in each CDR relative to the VH-CDR1, VH-CDR2 and VH-CDR3 sequences corresponding to SEQ ID NO:3, SEQ ID NO:4 and SEQ ID NO:5, respectively; a VL-CDR1, VL-CDR2 and/or VL CDR3 sequence identical to or identical to except for one, two, or three substitutions in each CDR relative to the VL-CDR1, VL-CDR2 and VL-CDR3 sequences corresponding to SEQ ID NO:6, SEQ ID NO:7 and SEQ ID NO:8, respectively; or VH-CDR1, VH-CDR2, VH CDR3, VL-CDR1, VL-CDR2 and VL CDR3 sequences identical to or identical to except for one, two, or three substitutions in each CDR relative to the VH-CDR1, VH-CDR2, VH CDR3, VL-CDR1, VL-CDR2 and VL CDR3 sequences corresponding to SEQ ID NO:3, SEQ ID NO:4 and SEQ ID NO:5, SEQ ID NO:6, SEQ ID NO:7 and SEQ ID NO: 8, respectively.

In particular embodiments, the isolated antibody or antigen-binding fragment thereof comprises a VH sequence at least 90%, 95% or 100% identical to the amino acid sequence of SEQ ID NO:1 and a VL sequence at least 90%, 95% or 100% identical to the amino acid sequence of SEQ ID NO:2.

In certain embodiments, an immunoconjugate, isolated antibody or antigen-binding fragment of the invention induces endocytosis of Siglec-15 at a rate where the half-life of endogenous surface Siglec-15 on human myelogenous leukemia K562 cells is less than about 5 minutes, less than about 4 minutes, or less than about 3 minutes In certain embodiments, an isolated antibody or antigen-binding fragment of the invention specifically binds to or competes with the same Siglec-15 epitope as an antibody or antigen-binding fragment as described above. In further embodiments, the isolated antibody or antigen-binding fragment of the invention specifically binds to the same Siglec-15 epitope as an antibody or antigen-binding fragment thereof comprising the VH and/or VL regions, or one or more CDR regions, of A9E8 or competitively inhibits Siglec-15 binding by an antibody or antigen-binding fragment thereof comprising the VH and/or VL regions, or one or more CDR regions, of A9E8.

In certain embodiments, an antibody or antigen-binding fragment of the invention is humanized, chimeric, fully human, a Fab fragment, a Fab' fragment, a F(ab)2 fragment, or a single chain Fv (scFv) fragment.

Also provided is a polypeptide comprising the VH and/or VL sequences or one or more of the CDR sequences of an antibody or antigen-binding fragment of the invention. In other embodiments, provided is an isolated cell producing the antibody, antigen-binding fragment, or polypeptide of the invention and a method of making the antibody, antigen-binding fragment, or polypeptide of the invention, comprising (a) culturing an isolated cell producing the antibody or antigen-binding fragment; and (b) isolating an antibody, antigen-binding fragment, or polypeptide from the cultured cell.

Also provided is an immunoconjugate having the formula (A)-(L)-(C) or (C)-(L)-(A), wherein: (A) is an antibody or antigen binding fragment thereof, or polypeptide of the invention; (L) is a linker; and (C) is a cytotoxic agent; and wherein the linker (L) links (A) to (C).

The invention further provides for a composition comprising an immunoconjugate, antibody, antigen-binding fragment, or polypeptide of the invention and a carrier.

Also provided is an isolated polynucleotide comprising a nucleic acid encoding a VH or VL as described above. In particular embodiments, the polynucleotide of the invention encodes an antibody comprising the nucleotide sequence SEQ ID NO:9 or SEQ ID NO:10. In further embodiments, provided is a vector comprising a polynucleotide of the invention.

Also provided is a method of treating acute myeloid leukaemia in a subject in need thereof, comprising administering to the subject an effective amount of an immunoconjugate, antibody, antigen-binding fragment or composition of the invention. In additional embodiments, a method of treating acute myeloid leukaemia reduces the number of leukemic stem cells.

Also provided is a method of reducing the side effects associated with treating acute myeloid leukaemia in a subject in need thereof comprising administering to the subject an effective amount of an immunoconjugate, antibody, antigen-binding fragment or composition of the invention. In certain embodiments, the side effect(s) are myelosuppression and/or hepatotoxicity.

Also provided is a method of reducing the number of blasts in an AML patient comprising administering to the patient an effective amount of an immunoconjugate, antibody, antigen-binding fragment or composition of the invention. In additional embodiments, the blasts are CD33+ or CD33−.

Also provided is a method of treating acute myeloid leukaemia in a subject having either low expression of CD33 or are CD33−, comprising administering to the subject an effective amount of an immunoconjugate, antibody, antigen-binding fragment or composition of the invention. In certain embodiments, the low expression is due to treatment with a CD33-targeted therapy.

Also provided is a method for making acute myeloid leukemia therapeutics comprising generating antibodies that bind Siglec-15, where the therapeutics preferentially target AML blasts over normal peripheral blood leukocytes. In particular embodiments, the antibodies according to this method are recombinant.

BRIEF DESCRIPTION OF THE DRAWINGS/FIGURES

FIG. 1: Siglec-15 transcript expression. (A) Four human Siglec-15 splice variants were identified by RT-PCR using specific primers. Electrophoresis of RT-PCR products from DAMI (megakaryocytic cell line), HEL (erythroleukaemic cell line) and K562 (erythroleukaemic cell line) are shown (left). Exon maps of the transcripts were generated after sequencing (right). Labelling reflects the number of extracellular immunoglobulin like domains contained in each splice variant, e.g. "2D" means 2 domains, etc. For the one domain "1D" splice variant, two isoforms were identified. "1D-A" encodes an extra short peptide from exon 2, which is lacking in "1D-B". (B) Results of RT-PCR analysis identifying a Siglec-15 transcript in 6 of 7 different cell lines tested. Only YT (natural killer-like leukaemic cell line) showed no Siglec-15 transcript. PMA or LPS stimulations over 48 hours up-regulated expression of the transcripts. GAPDH RT-PCR is shown underneath each panel to control for equal loading (0.4 kb). 293T cells were used as a negative control.

Figure 3:
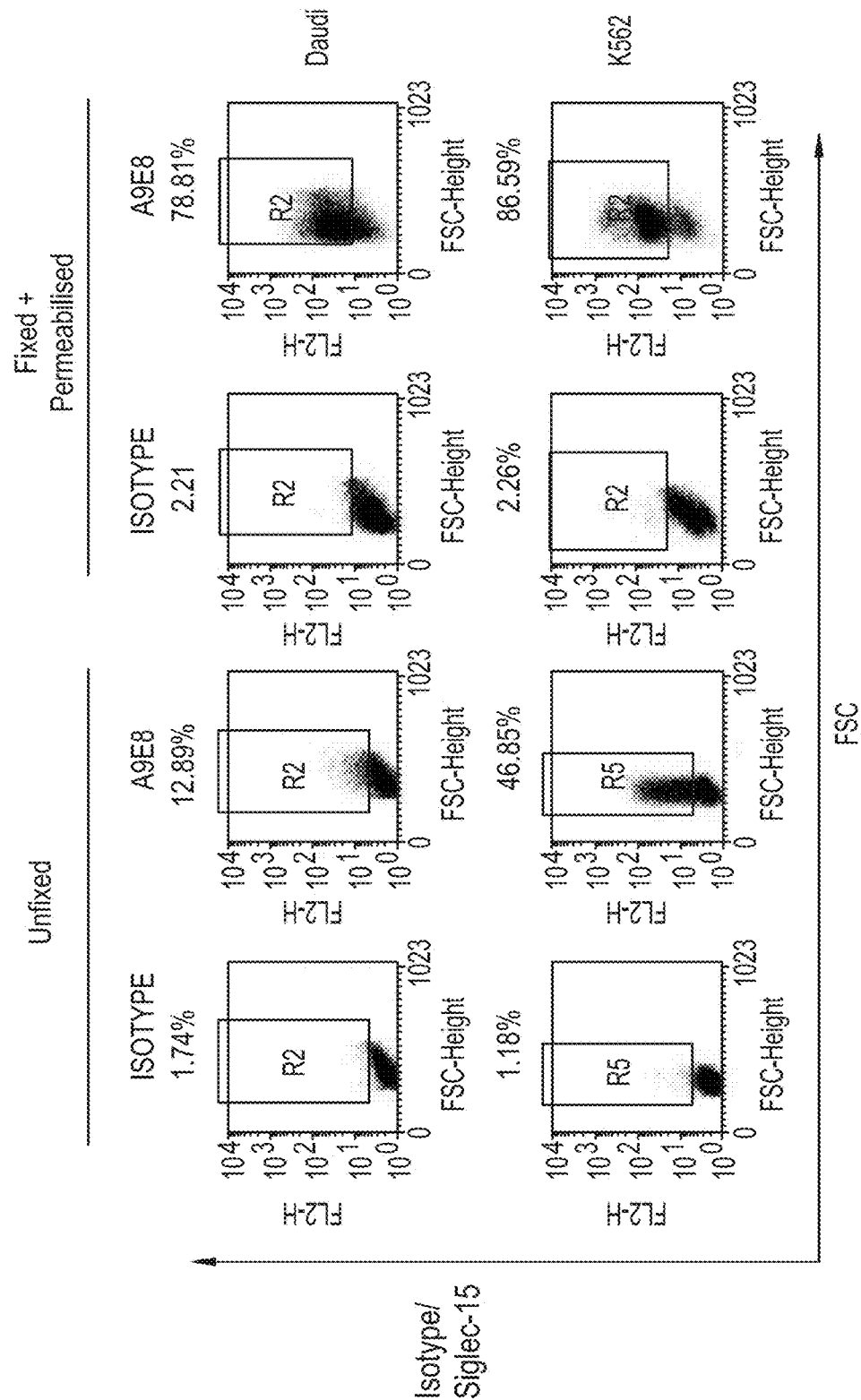

FIG. 2: Siglec-15-specific monoclonal antibodies. (A) Phage display technology was employed to select for clones expressing single chain fragment variable (ScFv) binders to purified Siglec-15 and also cell surface transfected Siglec-15. The variable domains (VH and VL) from two selected phage ScFv's were cloned into a mouse IgG1 antibody backbone and expressed as complete mouse IgG1 antibodies. The resultant monoclonal antibodies showed stronger binding to the CHO-pDisplay Siglec-15 stable cell line (unfilled histograms) than the parental CHO cell line (filled histograms) by flow cytometry. HA staining was used as a positive control. pDisplay constructs encode only the extracellular domains of Siglec-15 with N-terminal HA tag and a PDGFR transmembrane domain. (B) HEK-293 DAP10 stable cell lines were transiently transfected with full length FLAG-Siglec-15 for detection by confocal microscopy using monoclonal antibodies A9E8 and A4C9 (red). The cell surface marker, CD44 (rat antibody, blue) and endosomal marker, EEA1 (rabbit antibody, green) were used to define cell boundaries. Both antibodies stained similarly as compared to the positive control (mouse anti-FLAG monoclonal antibody). A HEK-293 expressing DAP10 stable cell line was used because the membrane adaptor molecule DAP10 facilitated surface expression of Siglec-15 (FIG. 3). (C) Specificity of A9E8 and A4C9 to Siglec-15 by FMAT (similar to confocal microscopy) comparing CHO stable cell lines encoding different Siglecs. ScFv versions of A9E8 and A4C9 bound specifically to the Siglec-15 CHO stable cell line. (D) Western blotting using A4C9 antibody. Lanes on the gel contain lysates of untransfected (UT) 293T cells and 293T cells transfected (T) with full length FLAG-Siglec-15 (right). The major band detected at ~43 kDa matches the size of fully glycosylated Siglec-15 and is sensitive to Endo-H digestion. Weak background bands were observed at ~50 kDa.

FIG. 3: Intracellular expression of Siglec-15. Daudi and K562 cells were subjected to FACS analysis for Siglec-15 expression using the A9E8 monoclonal antibody. FACS plots show forward scatter (FSC) on x-axis and either isotype or Siglec-15 (A9E8) staining on y-axis. Percentages indicate the proportion of live cell population with positive antibody staining levels above background (Rectangular gates). Unfixed staining shows surface expression (left), while fixed and permeabilized staining (right) reveal additional intracellular expression. For intracellular staining, cells were fixed first in paraformaldehyde (30 minutes, room temperature), washed three times in PBS and then permeabilized in 0.5% Triton-100 (10 minutes, room temperature) and washed for a further three times in PBS. Mouse IgG1 monoclonal isotype control antibody (Dako) was used in parallel. For unfixed cells, live cell gating was performed using SyTox Red (Invitrogen) staining.

Figure 4:
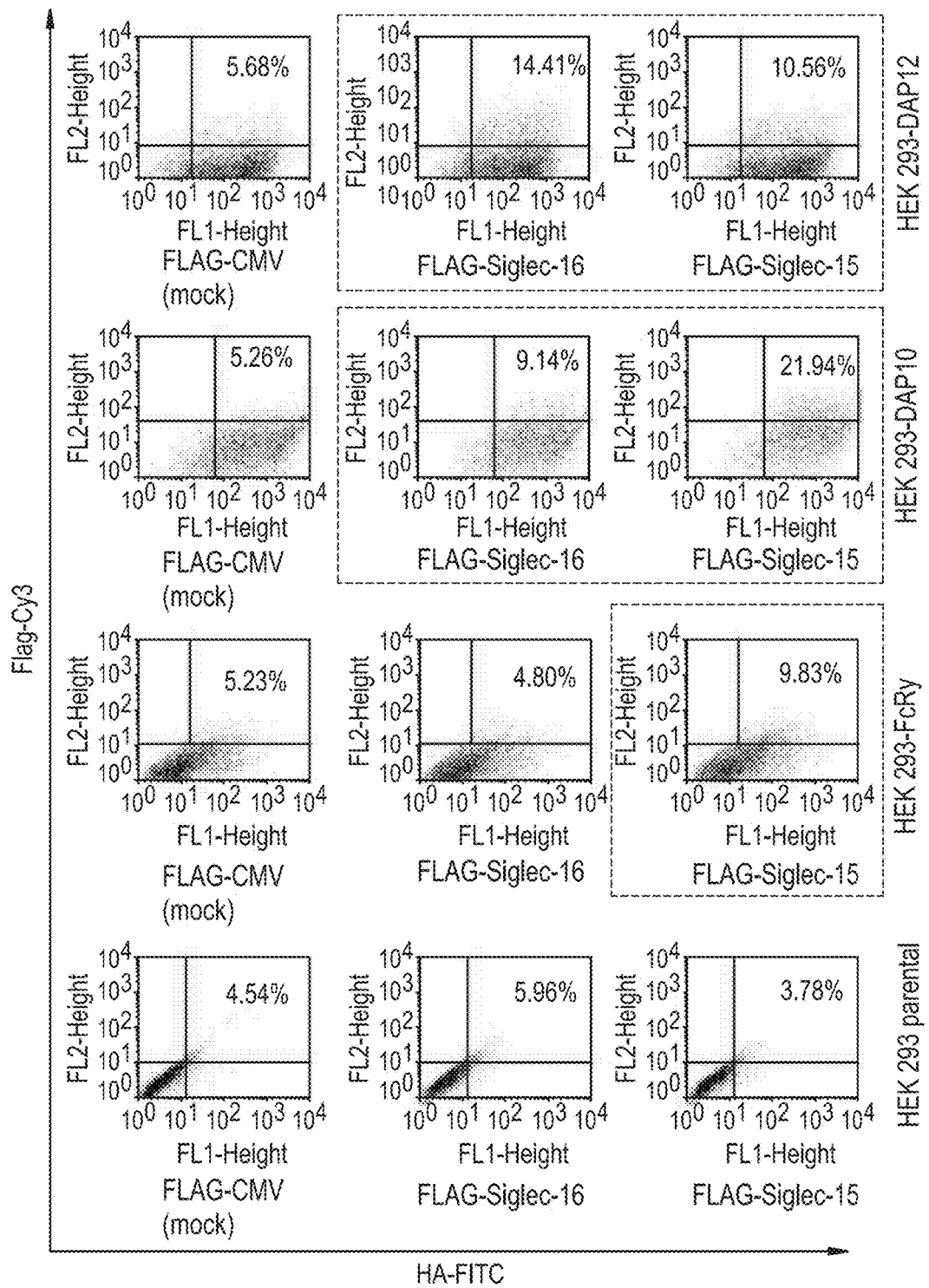

FIG. 4: Adaptor association of Siglec-15. FACS analysis of FLAG-tagged full length Siglec-15 and -16 expression on the surface of HEK-293 cells stably expressing different membrane adaptor molecules was assessed, each expressing N-terminal HA-tags. HA and Flag tags were co-stained. The x-axis shows surface adaptor expression levels (HA-FITC staining) and the y-axis shows surface Siglec expression (Flag-cy3) The percentage of double positive cells (shown in upper right quadrant) reflects adaptor dependent Siglec surface expression. Mock transfection was carried out using an empty FLAG-CMV vector. Untransfected HEK-293 cells were also used as a negative control. Adaptor and Siglec pairings which demonstrated increase in surface Siglec detection are boxed.

Figure 5:
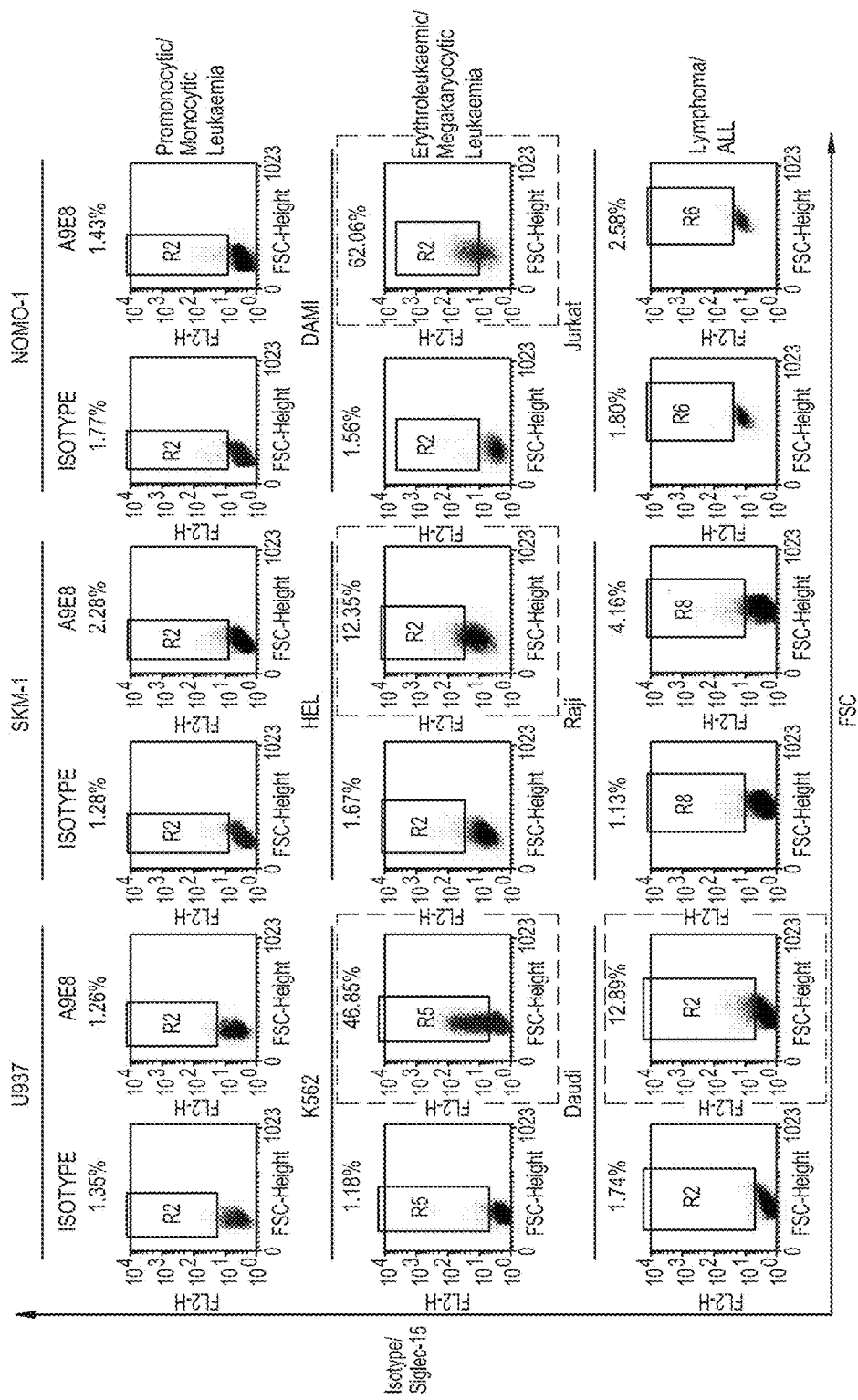

FIG. 5: Endogenous Siglec-15 surface expression on leukaemic cell lines. (A) FACS plots of surface Siglec-15 protein expression on leukaemic cell lines. The x-axis shows forward scatter (FSC) and the y-axis matched isotype control or Siglec-15 staining. A9E8 was used for Siglec-15 staining and mouse IgG1 monoclonal control antibody (Dako) as isotype control. Live cell gating was performed using SyTox Red (Invitrogen) staining. Percentages indicate the proportion of the live cell population staining positive at levels above background. Leukaemic cell lines of the myeloid lineage are shown in the first two rows. First row: monocytic (U937 and SKM-1) and promonocytic (NOMO-1) cell lines. Second row: erythroleukaemic (K562 and HEL) and megakaryocytic (DAMI) cell lines. Third row: B-cell lymphoma derived (Daudi and Raji) and T-cell acute lymphoblastic leukaemia (Jurkat) cell lines. (B) Western blot analysis of Siglec-15 cytoplasmic tail specific rabbit antisera (left) and mouse anti-FLAG monoclonal antibody staining of untransfected 293T cell lysates and lysates from 293T cells transfected with full length FLAG-Siglec-15 construct. A fully glycosylated Siglec-15 band was found at 43 kDa. (C) Western blot analysis of lysates from four leukaemic cell lines (K562, Raji, Jurkat and HEL) using both A4C9 monoclonal antibody that recognizes the extracellular domains of Siglec-15 and Tail 1A antisera that is specific for the cytoplasmic tail portion. Arrows indicate bands from both blots that match the ~43 kDa expected size for fully glycosylated Siglec-15.

FIG. 6: Siglec-15 is expressed only on a small number of a subset of healthy peripheral blood leukocytes. (A) Peripheral blood leukocytes obtained from healthy donors were used to analyse cell surface Siglec-15 expression on different leukocyte cell types. Murine IgG1 monoclonal antibody (Dako) was used as isotype control and different cell markers were used to differentiate between cell lineages: CD3 (T cells), CD19 (B cells), CD56(NK cells) and CD14 (monocytes). Live cells were gated by removing cells of low forward and side scatter values. Percentages indicate proportions of live cells in each quadrant. The X-axis corresponds to FITC labelled lineage marker staining and the y-axis corresponds to matched isotype control of Siglec-15 staining. No lineages stained for surface Siglec-15 except <4% of CD14+ monocytes (CD14). (B) Macrophages and dendritic cells were differentiated from peripheral blood monocytes and used for cell surface Siglec-15 detection. Markers (CD14 for macrophages and CD86) were used to ensure successful differentiation. Histograms show unstained (clear) and marker stained (red) macrophages and dendritic cells. FACS plots show forward scatter on the x-axis and either isotype or Siglec-15 (A9E8) staining on the y-axis. Percentages indicate the percentage of the population with positive staining above background levels. Macrophages and dendritic cells treated with or without LPS for 24 hours are labelled.

Figure 7:
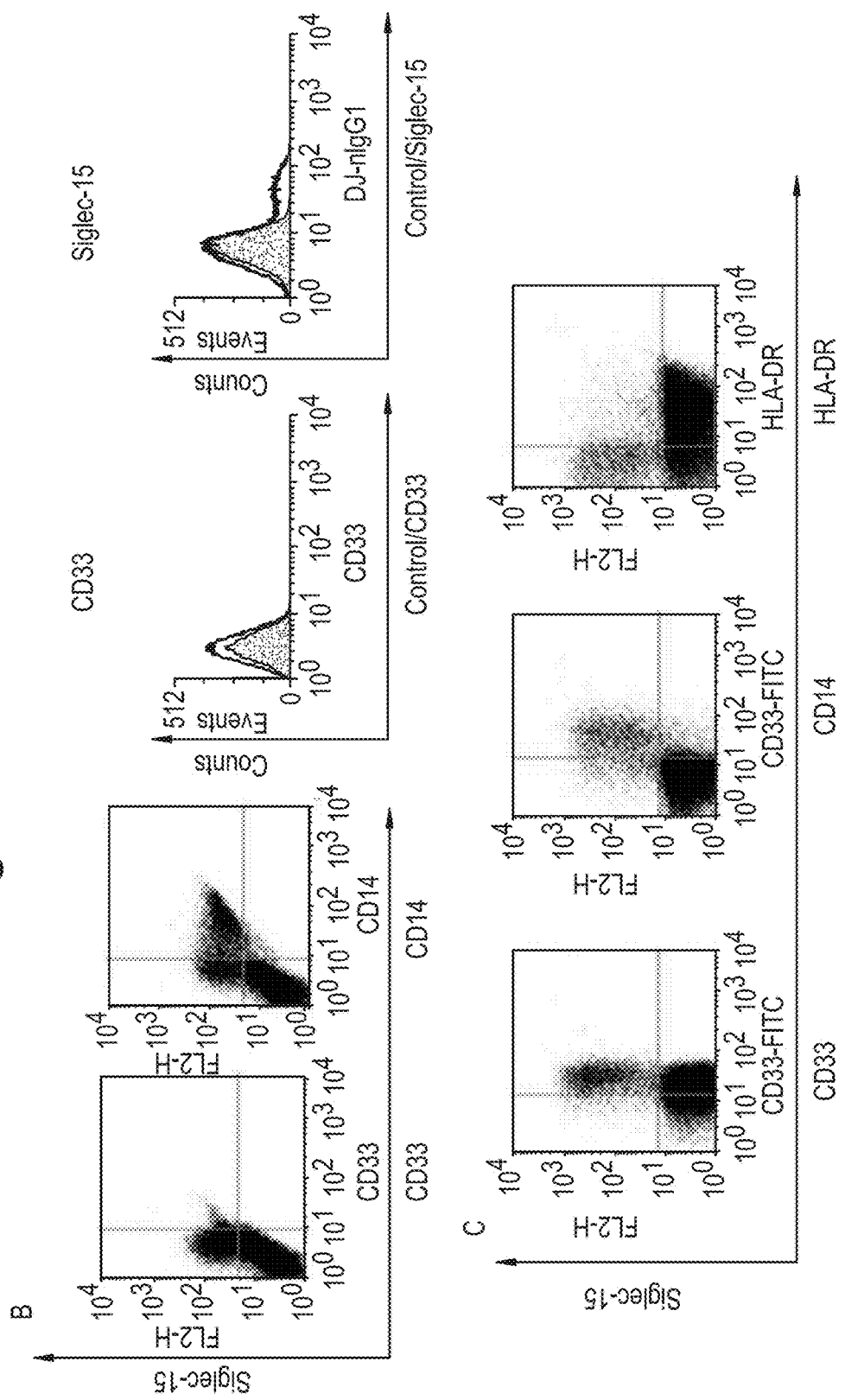
Figure 7:
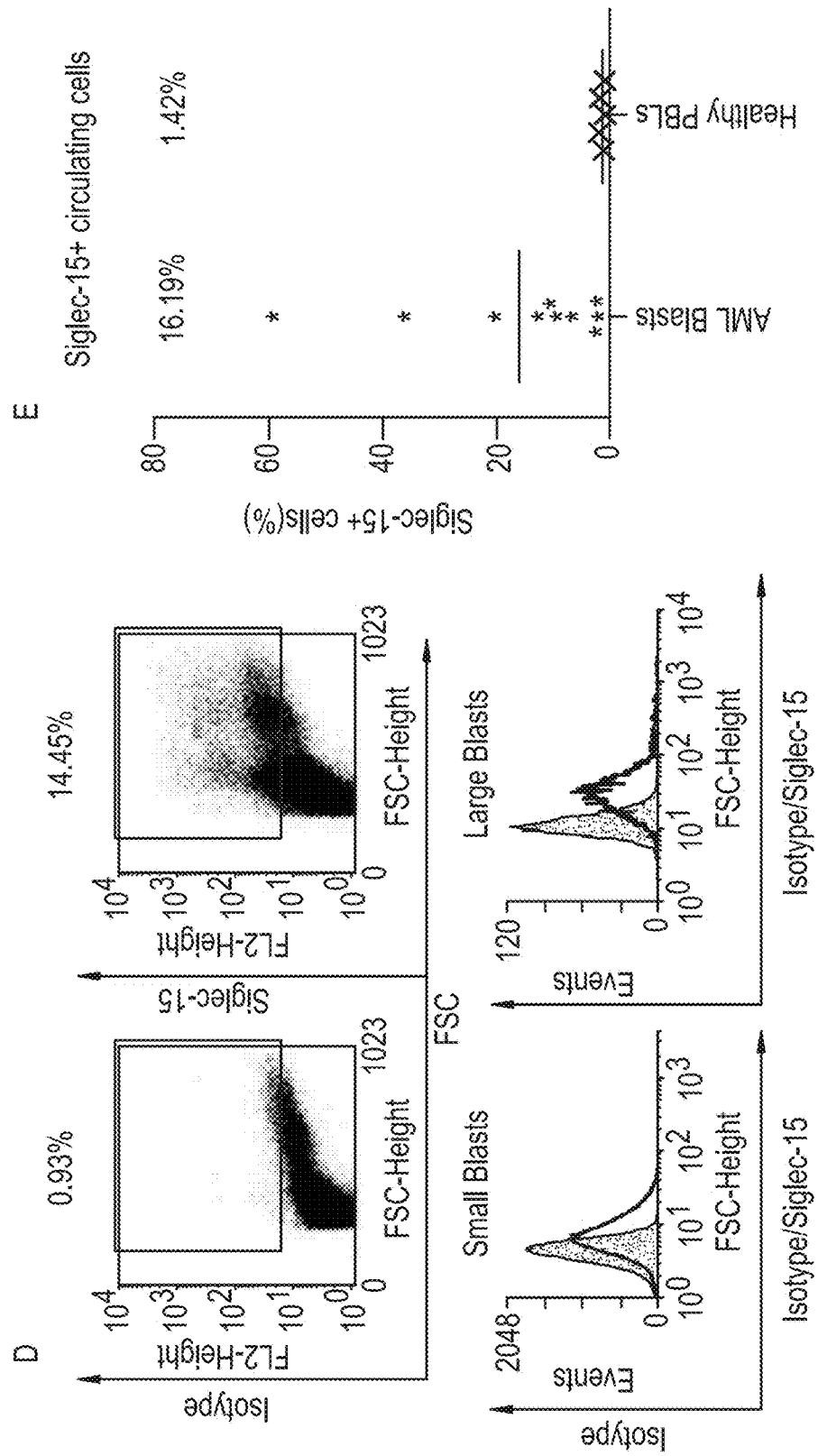

FIG. 7: High Siglec-15 surface expression on blasts from AML patients. AML patient blasts were used for studying surface Siglec-15 expression. Eight out of 10 patients showed significant Siglec-15 surface expression compared to healthy PBLs. Four examples are shown: (A) FACS analysis of cells from an individual AML patient (Patient A) showing high levels of Siglec-15 expression (35.7% of population), co-expressing with CD14 and HLA-DR. Mouse IgG1 isotype control was added for comparison. (B) FACS analysis of cells from a second AML patient (Patient B), showing that cells were negative for CD33 while exhibiting high Siglec-15 expression in 20.2% of the cell populations. Histograms compare CD33 expression (unstained—red, stained—clear) and Siglec-15 expression (unstained—red, stained—clear) on the same sample. (C) FACS analysis of cells from a third patient (Patient C) exhibited 10% Siglec-15 expressing blasts, most of which were CD33+CD14+ HLA-DR−. (D) FACS analysis of cells from a fourth patient (Patient D) had 14% Siglec-15 positive blasts. Histograms show difference in Siglec-15 surface staining for larger (higher forward scatter) and smaller (lower forward scatter) blasts (Isotype—red; Siglec-15—clear). (E) Summary of percentage of total circulating cells expressing Siglec-15 from either AML patients (dots) or Healthy donors (crosses). Horizontal lines indicate mean values.

FIG. 8: Endocytosis of surface Siglec-15. The rate of endocytosis for endogenously expressed surface Siglec-15 on K562 cells was measured by following loss of surface A9E8 binding upon incubation at 37° C. A9E8 staining was on ice for 30 minutes. Cells were then resuspended in serum-free media pre-warmed to 37° C. and incubated for varying lengths of time at 37° C. Time points varied from 30 seconds to 15 minutes. Isotype control antibody (mIgG1 control, Dako) was used to measure background staining/fluorescence. Mean fluorescence above isotype staining was calculated for different time points and expressed as a percentage of the maximum surface staining without incubation at 37° C. Plot (top) shows the fall of surface staining of Siglec-15 over 15 minutes; x-axis is time measured in seconds and y-axis is percentage of initial fluorescence. An exponential decay curve fits the data points well, corresponding to a half-life of 174 seconds. A parallel experiment was carried out using CHO cells stably expressing surface Siglec-15 in a pDisplay construct that lacks the natural Siglec-15 transmembrane domains and cytoplasmic tail and instead encodes a PDGFR transmembrane domain. Steady levels of surface staining (shown by line of best fit) for the CHO-Siglec-15 stable cell line demonstrates that A9E8 was not dissociating from the cell surface significantly during the first 15 minutes of incubation at 37° C.

DETAILED DESCRIPTION

I. Definitions

It is to be noted that the term "a" or "an" entity refers to one or more of that entity; for example, "an antibody which specifically binds to Siglec-15," is understood to represent one or more antibodies which specifically bind to Siglec-15. As such, the terms "a" (or "an"), "one or more," and "at least one" can be used interchangeably herein.

"Siglec-15" is a type-I transmembrane protein comprising two immunoglobulin-like domains, a transmembrane domain containing a lysine residue, and a short cytoplasmic tail. The extracellular domain of Siglec-15 preferentially recognizes Neu5Acα2-6GalNAcα structures and has immune system activating activity.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, but is not necessarily translated from a designated nucleic acid sequence. It can be generated in any manner, including by chemical synthesis.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides which have been separated, fractionated, or partially or substantially purified by any suitable technique.

Other polypeptides disclosed herein are fragments, derivatives, analogs, or variants of the foregoing polypeptides, and any combination thereof. The terms "fragment," "variant," "derivative" and "analog" when referring to an antibody which specifically binds to Siglec-15 as disclosed herein include any polypeptides which retain at least some of the antigen-binding properties of the corresponding native antibody or polypeptide. Fragments of polypeptides include, for example, proteolytic fragments, as well as deletion fragments, in addition to specific antibody fragments discussed elsewhere herein. Variants of an antibody which specifically binds to Siglec-15 as disclosed herein, include fragments as described above, and also polypeptides with altered amino acid sequences due to amino acid substitutions, deletions, or insertions. Variants can occur naturally or be non-naturally occurring. Non-naturally occurring variants can be produced using art-known mutagenesis techniques. Variant polypeptides can comprise conservative or non-conservative amino acid substitutions, deletions or additions. Derivatives of a an antibody or antigen-binding fragment which specifically binds to Siglec-15 as disclosed herein are polypeptides which have been altered so as to exhibit additional features not found on the native polypeptide. Examples include fusion proteins. Variant polypeptides can also be referred to herein as "polypeptide analogs." As used herein a "derivative" of an antibody or antigen-binding fragment which specifically binds to Siglec-15 refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody or antigen-binding fragment which specifically binds to Siglec-15 contained in a vector is considered isolated as disclosed herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can encode heterologous coding regions, either fused or unfused to a nucleic acid encoding an antibody, or antigen-binding fragment, variant, or derivative thereof which specifically binds to Siglec-15. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA).

Polynucleotide and nucleic acid coding regions can be associated with additional coding regions which encode secretory or signal peptides, which direct the secretion of a polypeptide encoded by a polynucleotide as disclosed herein, e.g., a polynucleotide encoding a antibody or antigen-binding fragment, or variant or derivative thereof which specifically binds to Siglec-15. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

Disclosed herein are certain antibodies, or antigen-binding fragments, variants, analogs or derivatives thereof including engineered antibody molecules or fragments that bind antigen in a manner similar to the antibody molecules as described. Also disclosed are immunoconjugates comprising such antibodies, or antigen-binding fragments, variants, analogs or derivatives thereof.

The terms "antibody" and "immunoglobulin" can be used interchangeably herein. An antibody (or a fragment, variant, or derivative thereof as disclosed herein comprises at least the variable domain of a heavy chain and at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG$_1$, IgG$_2$, IgG$_3$, IgG$_4$, IgA$_1$, etc. are well characterized and are known to confer functional specialization. Modified versions of each of these classes and isotypes are readily discernible to the skilled artisan in view of the instant disclosure and, accordingly, are within the scope of this disclosure.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody or antigen-binding fragment to selectively recognize and specifically bind epitopes on antigens. That is, the VL domain and VH domain, or subset of the complementarity determining regions (CDRs), of an antibody or antigen-binding fragment combine to form the variable region that defines a three dimensional antigen binding site. This quaternary antibody or antigen-binding fragment structure forms the antigen binding site present at the end of each arm of the Y. More specifically, the antigen binding site is defined by three CDRs on each of the VH and VL chains.

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, *J. Mol. Biol.*, 196:901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

|  | Kabat | Chothia |
| --- | --- | --- |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, or variant or derivative thereof which specifically binds to Siglec-15 as disclosed herein are according to the Kabat numbering system.

Antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds," it is generally meant that an antibody or fragment, variant, or derivative thereof binds to an epitope via its antigen binding domain, and that the binding entails some complementarity between the antigen binding domain and the epitope. According to this definition, an antibody or fragment, variant, or derivative thereof is said to "specifically bind" to an epitope when it binds to that epitope, via its antigen binding domain more readily than it would bind to a random, unrelated epitope. The term "specificity" is used herein to qualify the relative affinity by which a certain antibody or fragment, variant, or derivative thereof binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody can cross-react with the related epitope.

An antibody or fragment, variant, or derivative thereof, or an immunoconjugate comprising an antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. An antibody or fragment, variant, or derivative thereof can be said to competitively inhibit binding of the reference antibody or antigen binding fragment to a given epitope by at least 90%, at least 80%, at least 70%, at least 60%, or at least 50%.

Antibodies or antigen-binding fragments, variants or derivatives thereof as disclosed herein can also be described or specified in terms of their cross-reactivity. As used herein, the term "cross-reactivity" refers to the ability of an antibody or fragment, variant, or derivative thereof, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the Antibody fragments including single-chain antibodies can comprise the variable region(s) alone or in combination with the entirety or a portion of the following: hinge region, CH1, CH2, and CH3 domains. Also included are antibodies or antigen-binding fragments also comprising any combination of variable region(s) with a hinge region, CH1, CH2, and CH3 domains. Antibodies, or antigen-binding fragments thereof disclosed herein can be from any animal origin including birds and mammals. The antibodies can be human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described for example in, U.S. Pat. No. 5,939,598 by Kucherlapati et al.

As used herein, the term "heavy chain portion" includes amino acid sequences derived from an immunoglobulin heavy chain, an antibody or fragment, variant, or derivative thereof, comprising a heavy chain portion comprises at least one of: a CH1 domain, a hinge (e.g., upper, middle, and/or lower hinge region) domain, a CH2 domain, a CH3 domain, or a variant or fragment thereof. For example, an antibody or fragment, variant, or derivative thereof can comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, an antibody or fragment, variant, or derivative thereof comprises a polypeptide chain comprising a CH3 domain. Further, an antibody or fragment, variant, or derivative thereof for use in the disclosure can lack at least a portion of a CH2 domain (e.g., all or part of a CH2 domain). As set forth above, it will be understood by one of ordinary skill in the art that these domains (e.g., the heavy chain portions) can be modified such that they vary in amino acid sequence from the naturally occurring immunoglobulin molecule.

The heavy chain portions of an antibody or fragment, variant, or derivative thereof as disclosed herein can be derived from different immunoglobulin molecules. For example, a heavy chain portion of a polypeptide can comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. The light chain portion comprises at least one of a VL or CL domain.

Antibodies or antigen-binding fragments, variants, or derivatives thereof disclosed herein can be described or specified in terms of the epitope(s) or portion(s) of an antigen that they recognize or specifically bind. The portion of a target antigen which specifically interacts with the antigen binding domain of an antibody is an "epitope," or an "antigenic determinant." A target antigen, e.g., a polysaccharide can comprise a single epitope, but typically comprises at least two epitopes, and can include any number of epitopes, depending on the size, conformation, and type of antigen.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit. The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "chimeric antibody" will be held to mean any antibody wherein the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs can be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

The terms "fusion protein" or "chimeric protein" or descriptions of a protein or polypeptide comprising two moieties that are "fused," refer to a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A fusion protein can be created, for example, by chemical synthesis, or by creating and translating a polynucleotide in which the peptide regions are encoded in the desired relationship. As used herein, the terms "linked," "fused" or "fusion" are used interchangeably.

The term "immunoconjugate" or "conjugate" as used herein refers to a compound or a derivative thereof that is fused or linked to a cell binding agent (i.e., an anti-Siglec-15 antibody or fragment thereof) and is defined by a generic formula: C-L-A, wherein C=cytotoxin, L=linker, and A=cell binding agent or anti-Siglec-15 antibody or antibody fragment. Immunoconjugates can also be defined by the generic formula in reverse order: A-L-C. An "immunoconjugate" comprises a targeting portion, or moiety, such as an antibody or fragment thereof which retains antigen recognition capability, and an effector molecule, such as a therapeutic moiety or a detectable label.

An "immunotoxin" is an immunoconjugate in which the therapeutic moiety is a cytotoxin. A "targeting moiety" is the portion of an immunoconjugate intended to target the immunoconjugate to a cell of interest, e.g., an anti-Siglec-15 antibody or antigen-binding fragment thereof. Typically, the targeting moiety is an antibody, a scFv, a dsFv, an Fab, or an F(ab')$_2$. The targeting moiety can also comprise, e.g., a Fab', a Fd, V-NAR domain, an IgNar, an intrabody, an IgGΔCH2, a minibody, a F(ab')$_3$, a tetrabody, a triabody, a diabody, a single-domain antibody, DVD-Ig, Fcab, mAb$^2$, a (scFv)$_2$, or a scFv-Fc.

A "toxic moiety" is the portion of a immunotoxin which renders the immunotoxin cytotoxic to cells of interest.

A "therapeutic moiety" is the portion of an immunoconjugate intended to act as a therapeutic agent and in some embodiments can be a "toxic moiety."

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to therapeutic measures, wherein the object is to prevent or slow down (lessen) an undesired physiological change or disorder. Beneficial or desired clinical results include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on.

II. Antibodies or Antigen-Binding Fragments

Siglec-15 is a type-I transmembrane protein comprising two immunoglobulin-like domains, a transmembrane domain containing a lysine residue, and a short cytoplasmic tail. The extracellular domain of Siglec-15 preferentially recognizes Neu5Acα2-6GalNAcα structures and has immune system activating activity. Though previously identified on dendritic cells and macrophages, Siglec-15 is shown herein to be expressed in high levels on the surface of AML blasts and in low levels on peripheral blood leukocytes.

One embodiment is directed to an antibody or antigen-binding fragment thereof which specifically binds to Siglec-15. In certain embodiments, the antibody or antigen-binding fragment thereof is A9E8. In further embodiments, the antibody or antigen-binding fragment thereof is an immunoconjugate comprising a Siglec-15 antibody or antigen-binding fragment such as A9E8

The disclosure is further directed to an antibody or antigen-binding fragment thereof which specifically binds to the same Siglec-15 epitope as an antibody or antigen-binding fragment thereof comprising the heavy chain variable region (VH) and light chain variable region (VL) region of A9E8. Further included is an antibody or antigen-binding fragment thereof which specifically binds to Siglec-15 and competitively inhibits Siglec-15 binding by an antibody or antigen-binding fragment thereof comprising the A9E8 VH and/or VL; the A9E8 VH-CDR3 and/or A9E8 VL-CDR3; the A9E8 VH-CDR1, VH-CDR2, and VH-CDR3; the A9E8 VL-CDR1, VL-CDR2, and VL-CDR3; or the A9E8 VH-CDR1, VH-CDR2, VH-CDR3, VL-CDR1, VL-CDR2, and VL-CDR3. An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

Due to the differential expression of Siglec-15 on AML blasts as opposed to normal peripheral blood leukocytes, Siglec-15 can be used to screen for additional therapeutics, e.g., antibodies that bind Siglec-15 and immunoconjugates comprising the anti-Siglec-15 antibodies, that preferentially target AML blasts and have minimal effects on normal peripheral blood leukocytes. In one embodiment, the Siglec-15 therapeutic is an anti-Siglec-15 antibody or antigen-binding fragment. In another embodiment, the Siglec-15 therapeutic is an immunoconjugate comprising an anti-Siglec-15 targeting moiety. In a further embodiment, the Siglec-15 therapeutic is a small molecule.

Methods of making antibodies are well known in the art and described herein. Once antibodies to various fragments of, or to the full-length Siglec-15 without the signal sequence, have been produced, determining which amino acids, or epitope, of Siglec-15 to which the antibody or antigen binding fragment binds can be determined by epitope mapping protocols as described herein as well as methods known in the art (e.g. double antibody-sandwich ELISA as described in "Chapter 11—Immunology," *Current Protocols in Molecular Biology*, Ed. Ausubel et al., v.2, John Wiley & Sons, Inc. (1996)). Additional epitope mapping protocols can be found in Morris, G. *Epitope Mapping Protocols*, New Jersey: Humana Press (1996), which are both incorporated herein by reference in their entireties. Epitope mapping can also be performed by commercially available means (i.e. ProtoPROBE, Inc. (Milwaukee, Wis.)).

In certain aspects, the disclosure is directed to an antibody or fragment, variant, derivative or immunoconjugate thereof which specifically binds to Siglec-15 and induces an enhanced rate of Siglec-15 endocytosis. In certain embodiments, an antibody or fragment, variant, derivative or immunoconjugate thereof of the invention induces endocytosis of Siglec-15 at a rate where the half-life of surface endogenous Siglec-15 on human myelogenous leukemia K562 cells is less than about 5 minutes, about 4 minutes, about 3 minutes, about 2 minutes, about 1 minutes or about 30 seconds.

Unless it is specifically noted, as used herein a "fragment thereof" in reference to an antibody refers to an antigen-binding fragment, i.e., a portion of the antibody which specifically binds to the antigen.

Accordingly, certain embodiments disclosed herein include an anti-Siglec-15 antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies or antigen-binding fragment thereof described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

Modified forms of anti-Siglec-15 antibodies or antigen-binding fragments, variants, or derivatives thereof can be made from whole precursor or parent antibodies using techniques known in the art. Exemplary techniques are discussed elsewhere herein.

In certain embodiments both the variable and constant regions of anti-Siglec-15 antibodies or antigen-binding fragments are fully human. Fully human antibodies can be made using techniques that are known in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human anti bodies can likewise be produced by various display technologies, e.g., phage display or other viral display systems, as described in more detail elsewhere herein.

Anti-Siglec-15 antibodies or antigen-binding fragments thereof as disclosed herein can be made or manufactured using techniques that are known in the art. In certain embodiments, antibodies or fragments thereof are "recombinantly produced," i.e., are produced using recombinant DNA technology. Exemplary techniques for making antibody molecules or fragments thereof are discussed in more detail elsewhere herein.

In certain anti-Siglec-15 antibodies, the Fc portion can be mutated to decrease effector function using techniques known in the art. For example, the deletion or inactivation (through point mutations or other means) of a constant region domain can reduce Fc receptor binding of the circulating modified antibody thereby increasing tumor localization. In other cases it can be that constant region modifications moderate complement binding and thus reduce the serum half-life and nonspecific association of a conjugated cytotoxin. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as localization, biodistribution and serum half-life, can easily be measured and quantified using well known immunological techniques without undue experimentation.

In certain embodiments, anti-Siglec-15 antibodies or antigen-binding fragments, variants, immunoconjugates or derivatives thereof will not elicit a deleterious immune response in the animal to be treated, e.g., in a human. In one embodiment, anti-Siglec-15 antibodies or antigen-binding fragments, variants, immunoconjugates or derivatives thereof are modified to reduce their immunogenicity using art-recognized techniques. For example, antibodies can be humanized, de-immunized, or chimeric antibodies can be made. These types of antibodies are derived from a non-human antibody, typically a murine or primate antibody, that retains or substantially retains the antigen-binding properties of the parent antibody, but which is less immunogenic in humans. This can be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81:6851-6855 (1984); Morrison et al., *Adv. Immunol.* 44:65-92 (1988); Verhoeyen et al., *Science* 239:1534-1536 (1988); Padlan, *Molec. Immun.* 28:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, VH and VL sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of binding polypeptides, e.g., Siglec-15-specific antibodies or antigen-binding fragments thereof disclosed herein, which are then tested for function. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Anti-Siglec-15 antibodies or antigen-binding fragments, variants, immunoconjugates or derivatives thereof can be generated by any suitable method known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, Cold Spring Harbor Laboratory Press, 2nd ed. (1988)

DNA encoding antibodies or antibody fragments (e.g., antigen binding sites) can also be derived from antibody libraries, such as phage display libraries. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with scFv, Fab, Fv OE DAB (individual Fv region from light or heavy chains) or disulfide stabilized Fv antibody domains recombinantly fused to either the phage gene III or gene VIII protein. Exemplary methods are set forth, for example, in EP 368 684 B1; U.S. Pat. No. 5,969,108, Hoogenboom, H. R. and Chames, *Immunol. Today* 21:371 (2000); Nagy et al. *Nat. Med.* 8:801 (2002); Huie et al., *Proc. Natl. Acad. Sci.* USA 98:2682 (2001); Lui et al., *J. Mol. Biol.* 315:1063 (2002), each of which is incorporated herein by reference. Several publications (e.g., Marks et al., *Bio/Technology* 10:779-783 (1992)) have described the production of high affinity human antibodies by chain shuffling, as well as combinatorial infection and in vivo recombination as a strategy for constructing large phage libraries. In another embodiment, ribosomal display can be used to replace bacteriophage as the display platform (see, e.g., Hanes et al., *Nat. Biotechnol.* 18:1287 (2000); Wilson et al., *Proc. Natl. Acad. Sci.* USA 98:3750 (2001); or Irving et al., *J. Immunol. Methods* 248:31 (2001)). In yet another embodiment, cell surface libraries can be screened for antibodies (Boder et al., *Proc. Natl. Acad. Sci.* USA 97:10701 (2000); Daugherty et al., J. Immunol. Methods 243:211 (2000)). Such procedures provide alternatives to traditional hybridoma techniques for the isolation and subsequent cloning of monoclonal antibodies.

In phage display methods, functional antibody domains are displayed on the surface of phage particles which carry the polynucleotide sequences encoding them. For example, DNA sequences encoding VH and VL regions are amplified from animal cDNA libraries (e.g., human or murine cDNA libraries of lymphoid tissues) or synthetic cDNA libraries. In certain embodiments, the DNA encoding the VH and VL regions are joined together by an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 the VH or VL regions are usually recombinantly fused to either the phage gene III or gene VIII. Phage expressing an antigen binding domain that binds to an antigen of interest can be selected or identified with antigen, e.g., using labeled antigen or antigen bound or captured to a solid surface or bead.

Additional examples of phage display methods that can be used to make the antibodies include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references and in the examples below, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')$_2$ fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., *Methods in Enzymology* 203:46-88(1991); Shu et al., PNAS 90:7995-7999 (1993); and Skerra et al., *Science* 240:1038-1040 (1988).

Fully human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. In addition, various companies can be engaged to provide human antibodies produced in transgenic mice directed against a selected antigen using technology similar to that described above.

Fully human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 12:899-903 (1988). See also, U.S. Pat. No. 5,565,332.)

In another embodiment, DNA encoding desired monoclonal antibodies can be readily isolated and sequenced using conventional procedures (e.g., by using oligonucleotide probes that are capable of binding specifically to genes encoding the heavy and light chains of murine antibodies). Isolated and subcloned hybridoma cells or isolated phage, for example, can serve as a source of such DNA. Once isolated, the DNA can be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which can be synthetic as described herein) can be used to clone constant and variable region sequences for the manufacture antibodies as described in Newman et al., U.S. Pat. No. 5,658,570, filed Jan. 25, 1995, which is incorporated by reference herein. Transformed cells expressing the desired antibody can be grown up in relatively large quantities to provide clinical and commercial supplies of the immunoglobulin.

In one embodiment, an isolated antibody or antigen-binding fragment thereof comprises at least one heavy or light chain CDR of an antibody molecule, e.g., A9E8. In another embodiment, an isolated antibody or antigen-binding fragment thereof comprises at least two CDRs from one or more antibody molecules, e.g., A9E8. In another embodiment, an isolated antibody or antigen-binding fragment thereof comprises at least three CDRs from one or more antibody molecules, e.g., A9E8. In another embodiment, an isolated antibody or antigen-binding fragment thereof comprises at least four CDRs from one or more antibody molecules, e.g., A9E8. In another embodiment, an isolated antibody or antigen-binding fragment thereof comprises at least five CDRs from one or more antibody molecules, e.g., A9E8. In another embodiment, an isolated antibody or antigen-binding fragment thereof of the description comprises at least six CDRs from one or more antibody molecules, e.g., A9E8.

In a specific embodiment, the amino acid sequence of the heavy and/or light chain variable domains can be inspected to identify the sequences of the complementarity determining regions (CDRs) by methods that are well-known in the art, e.g., by comparison to known amino acid sequences of other heavy and light chain variable regions to determine the regions of sequence hypervariability. Using routine recombinant DNA techniques, one or more of the CDRs can be inserted within framework regions, e.g., into human framework regions to humanize a non-human antibody. The framework regions can be naturally occurring or consensus framework regions, and preferably human framework regions (see, e.g., Chothia et al., *J. Mol. Biol.* 278:457-479 (1998) for a listing of human framework regions). The polynucleotide generated by the combination of the framework regions and CDRs encodes an antibody that specifically binds to at least one epitope of a desired antigen, e.g., Siglec-15. One or more amino acid substitutions can be made within the framework regions, and, the amino acid substitutions improve binding of the antibody to its antigen. Additionally, such methods can be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present disclosure and are within the capabilities of a person of skill of the art.

Also provided are antibodies or antigen-binding fragments thereof that comprise, consist essentially of, or consist of, variants (including derivatives) of antibody molecules (e.g., the VH regions and/or VL regions) described herein, which antibodies or antigen-binding fragments specifically bind to Siglec-15. Standard techniques known to those of skill in the art can be used to introduce mutations in the nucleotide sequence encoding an antibody or antigen-binding fragment which specifically binds to Siglec-15, including, but not limited to, site-directed mutagenesis and PCR-mediated mutagenesis which result in amino acid substitutions. The variants (including derivatives) encode polypeptides comprising less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind Siglec-15).

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations can alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein can routinely be expressed and the functional and/or biological activity of the encoded protein, (e.g., ability to bind at least one epitope of Siglec-15) can be determined using techniques described herein or by routinely modifying techniques known in the art.

III. Antibody Polypeptides and Immunoconjugates

The disclosure is further directed to isolated polypeptides which make up antibodies or antigen-binding fragments thereof, which specifically bind to Siglec-15 and polynucleotides encoding such polypeptides. Isolated antibodies or fragments thereof as disclosed herein, comprise polypeptides, e.g., amino acid sequences encoding, for example, Siglec-15-specific antigen binding regions derived from immunoglobulin molecules. A polypeptide or amino acid sequence "derived from" a designated protein refers to the origin of the polypeptide. In certain cases, the polypeptide or amino acid sequence which is derived from a particular starting polypeptide or amino acid sequence has an amino acid sequence that is essentially identical to that of the starting sequence, or a portion thereof, wherein the portion consists of at least 10-20 amino acids, at least 20-30 amino acids, at least 30-50 amino acids, or which is otherwise identifiable to one of ordinary skill in the art as having its origin in the starting sequence.

Also disclosed is an isolated antibody or antigen-binding fragment thereof which specifically binds to Siglec-15 comprising an immunoglobulin heavy chain variable region (VH) amino acid sequence at least 80%, 85%, 90% 95% or 100% identical to SEQ ID NO: 1 as shown in Table 1.

Further disclosed is an isolated antibody or antigen-binding fragment thereof which specifically binds to Siglec-15 comprising a VH amino acid sequence identical to, or identical except for one, two, three, four, five, or more amino acid substitutions to SEQ ID NO: 1 as shown in Table 1.

Also disclosed is an isolated antibody or antigen-binding fragment thereof which specifically binds to Siglec-15 comprising an immunoglobulin light chain variable region (VL) amino acid sequence at least 80%, 85%, 90% 95% or 100% identical to SEQ ID NO: 2 as shown in Table 1.

Some embodiments disclose an isolated antibody or antigen-binding fragment thereof which specifically binds to Siglec-15 comprising a VL amino acid sequence identical to, or identical except for one, two, three, four, five, or more amino acid substitutions to SEQ ID NO: 2 as shown in Table 1.

Also disclosed is an isolated antibody or antigen-binding fragment thereof which specifically binds to Siglec-15 comprising a VH-CDR1, VH-CDR2 and/or VH-CDR3, where the VH-CDR1, VH-CDR2 and VH-CDR3 correspond to SEQ ID NO: 3, SEQ ID NO:4 and SEQ ID NO: 5, respectively. In further embodiments, the isolated antibody or antigen-binding fragment thereof comprises a VL-CDR1, VL-CDR2 and/or VL-CDR3, where the VL-CDR1, VL-CDR2 and VL-CDR3 correspond to SEQ ID NO: 6, SEQ ID NO:7 and SEQ ID NO: 8, respectively. In particular embodiments, the isolated antibody or antigen-binding fragment thereof comprises a VH-CDR1, VH-CDR2 VH-CDR3, VL-CDR1, VL-CDR2 and/or VL-CDR3, where the VH-CDR1, VH-CDR2 VH-CDR3, VL-CDR1, VL-CDR2 and VL-CDR3 correspond to SEQ ID NO: 3, SEQ ID NO:4, SEQ ID NO: 5. SEQ ID NO: 6, SEQ ID NO:7 and SEQ ID NO: 8, respectively.

Also disclosed is an isolated antibody or antigen-binding fragment thereof which specifically binds to Siglec-15 comprising a VH-CDR1, VH-CDR2 and/or VH-CDR3; a VL-CDR1, VL-CDR2 and/or VL-CDR3; or a VH-CDR1, VH-CDR2, VH-CDR3, VL-CDR1, VL-CDR2 and/or VL-CDR3; where the sequence of each CDR is identical to, or identical to except for one, two or three amino acid substitutions in each CDR relative to the VH-CDR1, VH-CDR2, VH-CDR3, VL-CDR1, VL-CDR2 and VL-CDR3 sequences corresponding to SEQ ID NO: 3, SEQ ID NO:4, SEQ ID NO: 5. SEQ ID NO: 6, SEQ ID NO:7 and SEQ ID NO: 8, respectively.

In certain embodiments, an isolated antibody or antigen-binding fragment thereof as described herein specifically binds to Siglec-15 and causes an increased rate of endocytosis of the receptor. In some embodiments, the half-life of Siglec-15 endocytosis is less than about 5 minutes, about 4 minutes, about 3 minutes, about 2 minutes, about 1 minutes or about 30 seconds in the human myelogenous leukemia cell line K562.

that they vary in amino acid sequence from the naturally occurring binding polypeptide from which they were derived. For example, a polypeptide or amino acid sequence derived from a designated protein can be similar, e.g., have a certain percent identity to the starting sequence, e.g., it can be 60%, 70%, 75%, 80%, 85%, 90%, or 95% identical to the starting sequence.

As known in the art, "sequence identity" between two polypeptides is determined by comparing the amino acid sequence of one polypeptide to the sequence of a second polypeptide. When discussed herein, whether any particular polypeptide is at least about 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence, the parameters are set, of course, such that the percentage of identity is calculated over the full length of the reference polypeptide

TABLE 1

Reference VH and VL amino acid sequences

| Antibody Name | VH | VH-CDR1 | VH-CDR2 | VH-CDR3 |
|---|---|---|---|---|
| A9E8 | QLQLQESGPGLVKPSETL SLTCAVSGASISNWWSWV RQPPGKGLEWIGEVHHSG VTTYKPSLKSRVTISVDN SKNQLSLKLTSVTAADTA VYYCAREFADDAFDIWGR GTMVTVSS (SEQ ID NO: 1) | NWWS (SEQ ID NO: 3) | EVHHSGVT TYKPSLKS (SEQ ID NO: 4) | EFADDAFDI (SEQ ID NO: 5) |

| Antibody Name | VL | VL-CDR1 | VL-CDR2 | VL-CDR3 |
|---|---|---|---|---|
| A9E8 | SSELTQDPAVSVALGQTV RITCRGDSLRKYYASWYQ QKPRQAPQLVIYHKNNRA SGIPDRFSGSISGNTASL TITGAQAEDEAAYFCNSR DTSGNYLVFGGGTKVTVL G (SEQ ID NO: 2) | RGDSLRKY YAS (SEQ ID NO: 6) | HKNNRAS (SEQ ID NO: 7) | NSRDTSGN YLV (SEQ ID NO: 8) |

Any anti-Siglec-15 antibodies or fragments, variants or derivatives thereof described herein can further include additional polypeptides, e.g., a signal peptide to direct secretion of the encoded polypeptide, antibody constant regions as described herein, or other heterologous polypeptides as described herein. Additionally, antibodies or fragments thereof of the description include polypeptide fragments as described elsewhere. Additionally anti-Siglec-15 antibodies or fragments, variants or derivatives thereof described herein can be fusion polypeptides, Fab fragments, scFvs, or other derivatives, as described herein.

Also, as described in more detail elsewhere herein, the disclosure includes compositions comprising anti-Siglec-15 antibodies or fragments, variants or derivatives thereof described herein.

It will also be understood by one of ordinary skill in the art that anti-Siglec-15 antibodies or fragments, variants or derivatives thereof described herein can be modified such sequence and that gaps in homology of up to 5% of the total number of amino acids in the reference sequence are allowed.

Furthermore, nucleotide or amino acid substitutions, deletions, or insertions leading to conservative substitutions or changes at "non-essential" amino acid regions can be made. For example, a polypeptide or amino acid sequence derived from a designated protein can be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

An anti-Siglec-15 antibody or fragment, variant or derivative thereof described herein can comprise, consist essentially of, or consist of a fusion protein. Fusion proteins are chimeric molecules which comprise, for example, an immunoglobulin antigen-binding domain with at least one target binding site, and at least one heterologous portion, i.e., a portion with which it is not naturally linked in nature. The amino acid sequences can normally exist in separate proteins that are brought together in the fusion polypeptide or they can normally exist in the same protein but are placed in a new arrangement in the fusion polypeptide. Fusion proteins can be created, for example, by chemical synthesis, or by creating and translating a polynucleotide in which the peptide regions are encoded in the desired relationship.

The term "heterologous" as applied to a polynucleotide, polypeptide, or other moiety means that the polynucleotide, polypeptide, or other moiety is derived from a distinct entity from that of the rest of the entity to which it is being compared. In a non-limiting example, a "heterologous polypeptide" to be fused to an antibody or an antigen-binding fragment, variant, or derivative thereof is derived from a non-immunoglobulin polypeptide of the same species, or an immunoglobulin or non-immunoglobulin polypeptide of a different species.

Toxins can be employed with antibodies or polypeptides of the present invention to yield immunoconjugates. Exemplary toxins include ricin, abrin, diptheria toxin and subunits thereof, as well as botulinum toxins A through F. These toxins are readily available from commercial sources (e.g., Sigma Chemical Company, St. Louis, Mo.). Diptheria toxin is isolated from *Corynebacterium diphtheriae*. Ricin is the lectin RCA60 from *Ricinus communes* (Castor bean). The term also references toxic variants thereof. See, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65,000 and 120,000, respectively. Nicholson and Blaustein, *J. Biochim. Biophys. Acta,* 266:543 (1972). The A chain is responsible for inactivating protein synthesis and killing cells. The B chain binds ricin to cell-surface galactose residues and facilitates transport of the A chain into the cytosol (Olsnes et al., *Nature,* 1974; 249:627-631). See, U.S. Pat. No. 3,060,165.

In one embodiment, the toxin is *Pseudomonas* exotoxin. *Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The *Pseudomonas* exotoxins (PE) can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (e.g., as a protein or pre-protein). Cytotoxic fragments of PE include PE40, PE38, and PE35. PE40 is a truncated derivative of PE as previously described in the art. See, Pai et al., *Proc. Natl. Acad. Sci. USA,* 88:3358-62 (1991); Kondo et al., *J. Biol. Chem.* 263:9470-9475 (1988). PE38 is a truncated PE composed of amino acids 253-364 and 381-613. PE35 is a 35 kD carboxyl-terminal fragment of PE composed of a Met at position 280 followed by amino acids 281-364 and 381-613 of native PE. In preferred embodiments, the cytotoxic fragment PE38 is employed. PE38 is a pro-protein which can be activated to its cytotoxic form upon processing within a cell.

With the *Pseudomonas* exotoxins and antibodies herein provided, one of skill can readily construct a variety of clones containing functionally equivalent nucleic acids, such as nucleic acids which differ in sequence but which encode the same PE or antibody sequence. Thus, the present invention provides nucleic acids encoding antibodies and conjugates and fusions thereof.

In other embodiments the toxin is a holotoxin (e.g., a ribosome inactivating protein type II) or a hemitoxin (e.g., saporin, gelonin). In further embodiments, the toxin is a cytotoxic agent or compound, examples of which include taxanes, DNA-alkylating agents, anthracyclines, microtubule inhibitors (e.g., tubulysins), duocarmycins, maytansinoids, doxorubicin and auristatins.

IV. Polynucleotides Encoding Antibodies or Antigen-Binding Fragments Thereof

Also provided herein are nucleic acid molecules encoding the anti-Siglec-15 antibodies or fragments, variants or derivatives thereof described herein.

One embodiment provides an isolated polynucleotide comprising, consisting essentially of, or consisting of a nucleic acid encoding an immunoglobulin heavy chain variable region (VH) amino acid sequence at least 80%, 85%, 90% 95% or 100% identical to SEQ ID NO: 1 as shown in Table 1.

Another embodiment provides an isolated polynucleotide comprising, consisting essentially of, or consisting of a nucleic acid encoding a VH amino acid sequence identical to, or identical except for one, two, three, four, five, or more amino acid substitutions to SEQ ID NO: 1 as shown in Table 1.

A further embodiment provides an isolated antibody or antigen-binding fragment comprising the VH encoded by the polynucleotide specifically or preferentially binds to Siglec-15.

Another embodiment provides an isolated polynucleotide comprising, consisting essentially of, or consisting of a nucleic acid encoding an immunoglobulin light chain variable region (VL) amino acid sequence at least 80%, 85%, 90% 95% or 100% identical to SEQ ID NO: 2 as shown in Table 1.

A further embodiment provides an isolated polynucleotide comprising, consisting essentially of, or consisting of a nucleic acid encoding a VL amino acid sequence identical to, or identical except for one, two, three, four, five, or more amino acid substitutions to SEQ ID NO: 2 as shown in Table 1.

In another embodiment, an isolated antibody or antigen-binding fragment comprising the VL encoded by the polynucleotide specifically or preferentially binds to Siglec-15.

One embodiment provides an isolated polynucleotide comprising, consisting essentially of, or consisting of a nucleic acid at least 80%, 85%, 90% 95% or 100% identical to SEQ ID NO: 9 or SEQ ID NO:10 as shown in Table 2.

TABLE 2

Reference nucleic acid sequences

| Antibody Name | nucleotide sequences |
|---|---|
| A9E8-VH | CAGCTGCAGCTGCAGGAGTCGGGCCCAGGACTGGTGAAGC<br>CTTCGGAAACCCTGTCCCTCACCTGCGCTGTCTCTGGTGC<br>CTCCATTAGTAACTGGTGGACTTGGGTCCGCCAGCCCCCA<br>GGGAAGGGGCTGGAGTGGATTGGGGAAGTCCATCATAGTG |

TABLE 2-continued

Reference nucleic acid sequences

| Antibody Name | nucleotide sequences |
|---|---|
| | GAGTCACCACCTACAAGCCGTCCCTCAAGAGTCGAGTCAC<br>CATATCAGTAGACAACTCGAAGAACCAATTATCTCTGAAG<br>CTAACCTCTGTGACAGCCGCGGACACGGCCGTGTATTACT<br>GTGCGAGAGAGTTCGCGGATGATGCTTTTGATATCTGGGG<br>CCGAGGGACAATGGTCACCGTCTCGAGT<br>(SEQ ID NO: 9) |
| A9E8-VL | TCTTCTGAGCTGACTCAGGACCCTGCTGTGTCTGTGGCCT<br>GGGACAGACAGTCAGGATCACATGCCGAGGGGACAGCCTC<br>TAGAAAGTATATGCAAGCTGGTACCAGCAGAAGCCACGAC<br>AGGCCCCTCAACTTGTCATCTATCATAAAAACAACAGGGC<br>GTCAGGGATCCCAGACCGATTCTCTGGCTCCATCTCCGGA<br>AACACAGCTTCTTTGACCATCACTGGGGCTCAGGCAGAAG<br>ATGAGGCTGCCTATTTCTGTAATTCTCGGGACACCAGTGG<br>TAATTATCTGGTCTTCGGCGGAGGGACCAAGGTCACCGTC<br>CTAGGT (SEQ ID NO: 10) |

In some embodiments, an isolated antibody or antigen-binding fragment thereof encoded by one or more of the polynucleotides described above, which specifically binds to Siglec-15, comprises, consists essentially of, or consists of VH and VL amino acid sequences at least 80%, 85%, 90% 95% or 100% identical to SEQ ID NO: 1 and SEQ ID NO: 2, respectively.

The disclosure also includes fragments of the polynucleotides as described elsewhere herein. Additionally polynucleotides which encode fusion polynucleotides, Fab fragments, and other derivatives, as described herein, are also provided.

The polynucleotides can be produced or manufactured by any method known in the art. For example, if the nucleotide sequence of the antibody is known, a polynucleotide encoding the antibody can be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an anti-Siglec-15 antibody or fragment, variant or derivative thereof can be generated from nucleic acid from a suitable source. If a clone containing a nucleic acid encoding a particular antibody is not available, but the sequence of the antibody molecule is known, a nucleic acid encoding the antibody can be chemically synthesized or obtained from a suitable source (e.g., an antibody cDNA library, or a cDNA library generated from, or nucleic acid, preferably poly A+RNA, isolated from, any tissue or cells expressing the antibody or such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

Once the nucleotide sequence and corresponding amino acid sequence of an anti-Siglec-15 antibody or fragment, variant or derivative thereof is determined, its nucleotide sequence can be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning, A Laboratory Manual*, 2d Ed., Cold Spring Harbor Laboratory, Cold Spring Harbor, N.Y. (1990) and Ausubel et al., eds., *Current Protocols in Molecular Biology*, John Wiley & Sons, NY (1998), which are both incorporated by reference herein in their entireties), to generate antibodies having a different amino acid sequence, for example to create amino acid substitutions, deletions, and/or insertions.

A polynucleotide encoding an anti-Siglec-15 antibody or fragment, variant or derivative thereof can be composed of any polyribonucleotide or polydeoxribonucleotide, which can be unmodified RNA or DNA or modified RNA or DNA. For example, a polynucleotide encoding an anti-Siglec-15 antibody or fragment, variant or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, a polynucleotide encoding an anti-Siglec-15 antibody or fragment, variant or derivative thereof can be composed of triple-stranded regions comprising RNA or DNA or both RNA and DNA. A polynucleotide encoding an anti-Siglec-15 antibody or fragment, variant or derivative thereof can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations can be introduced by standard techniques, such as site-directed mutagenesis and PCR-mediated mutagenesis. Conservative amino acid substitutions are made at one or more non-essential amino acid residues.

V. Expression of Antibody Polypeptides

As is well known, RNA can be isolated from the original hybridoma cells or from other transformed cells by standard techniques, such as guanidinium isothiocyanate extraction and precipitation followed by centrifugation or chromatography. Where desirable, mRNA can be isolated from total RNA by standard techniques such as chromatography on oligo dT cellulose. Suitable techniques are familiar in the art.

In one embodiment, cDNAs that encode the light and the heavy chains of the anti-Siglec-15 antibody or fragment, variant or derivative thereof can be made, either simultaneously or separately, using reverse transcriptase and DNA polymerase in accordance with well-known methods. PCR can be initiated by consensus constant region primers or by more specific primers based on the published heavy and light chain DNA and amino acid sequences. As discussed above, PCR also can be used to isolate DNA clones encoding the antibody light and heavy chains. In this case the libraries can be screened by consensus primers or larger homologous probes, such as mouse constant region probes.

DNA, typically plasmid DNA, can be isolated from the cells using techniques known in the art, restriction mapped and sequenced in accordance with standard, well known techniques set forth in detail, e.g., in the foregoing references relating to recombinant DNA techniques. Of course, the DNA can be synthetic according to the present disclosure at any point during the isolation process or subsequent analysis.

Following manipulation of the isolated genetic material to provide an anti-Siglec-15 antibody or fragment, variant or derivative thereof of the disclosure, the polynucleotides encoding anti-Siglec-15 antibodies or antigen-binding fragments thereof are typically inserted in an expression vector for introduction into host cells that can be used to produce the desired quantity of anti-Siglec-15 antibodies or antigen-binding fragments thereof.

Recombinant expression of an antibody, or fragment, derivative or analog thereof, e.g., a heavy or light chain of an antibody which binds to a target molecule described herein, e.g., Siglec-15, requires construction of an expression vector containing a polynucleotide that encodes the antibody. Once a polynucleotide encoding an antibody molecule or a heavy or light chain of an antibody, or portion thereof (containing the heavy or light chain variable domain), of the disclosure has been obtained, the vector for the production of the antibody molecule can be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The disclosure, thus, provides replicable vectors comprising a nucleotide sequence encoding an antibody molecule of the disclosure, or a heavy or light chain thereof, or a heavy or light chain variable domain, operably linked to a promoter. Such vectors can include the nucleotide sequence encoding the constant region of the antibody molecule (see, e.g., PCT Publication WO 86/05807; PCT Publication WO 89/01036; and U.S. Pat. No. 5,122,464) and the variable domain of the antibody can be cloned into such a vector for expression of the entire heavy or light chain.

The term "vector" or "expression vector" is used herein to mean vectors used in accordance with the present disclosure as a vehicle for introducing into and expressing a desired gene in a host cell. As known to those skilled in the art, such vectors can easily be selected from the group consisting of plasmids, phages, viruses and retroviruses. In general, vectors compatible with the instant disclosure will comprise a selection marker, appropriate restriction sites to facilitate cloning of the desired gene and the ability to enter and/or replicate in eukaryotic or prokaryotic cells.

For the purposes of this disclosure, numerous expression vector systems can be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements can also be needed for optimal synthesis of mRNA. These elements can include signal sequences, splice signals, as well as transcriptional promoters, enhancers, and termination signals.

In some embodiments the cloned variable region genes are inserted into an expression vector along with the heavy and light chain constant region genes (e.g., human) synthetic as discussed above. Of course, any expression vector which is capable of eliciting expression in eukaryotic cells can be used in the present disclosure. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems.

More generally, once the vector or DNA sequence encoding a monomeric subunit of the anti-Siglec-15 antibody or fragment, variant or derivative thereof of the disclosure has been prepared, the expression vector can be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Vectors, Rodriguez and Denhardt, Eds., Butterworths, Boston, Mass., Chapter 24.2, pp. 470-472 (1988). Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the disclosure includes host cells containing a polynucleotide encoding anti-Siglec-15 antibody or fragment, variant or derivative thereof, or a heavy or light chain thereof, operably linked to a heterologous promoter. In some embodiments for the expression of double-chained antibodies, vectors encoding both the heavy and light chains can be co-expressed in the host cell for expression of the entire immunoglobulin molecule, as detailed below.

Certain embodiments include an isolated polynucleotide comprising a nucleic acid which encodes the above-described VII and VI, wherein an antibody or antigen-binding fragment thereof expressed by the polynucleotide specifically binds Siglec-15. In some embodiments the polynucleotide as described encodes an scFv molecule including VH and VL, at least 80%, 85%, 90% 95% or 100% identical to SEQ ID NO:9 or SEQ ID NO:10as shown in Table 2.

Some embodiments include vectors comprising the above-described polynucleotides. In further embodiments, the polynucleotides are operably associated with a promoter. In additional embodiments, the disclosure provides host cells comprising such vectors. In further embodiments, the disclosure provides vectors where the polynucleotide is operably associated with a promoter, wherein vectors can express an antibody or antigen-binding fragment thereof which specifically binds Siglec-15 in a suitable host cell.

Also provided is a method of producing an antibody or fragment thereof which specifically binds Siglec-15, comprising culturing a host cell containing a vector comprising the above-described polynucleotides, and recovering said antibody, or fragment thereof. In further embodiments, the disclosure provides an isolated antibodies or fragments thereof produced by the above-described method.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" can mean either from spun down whole cells, or from the cell culture containing both the medium and the suspended cells.

A variety of host-expression vector systems can be utilized to express antibody molecules for use in the methods described herein. Such host-expression systems represent vehicles by which the coding sequences of interest can be produced and subsequently purified, but also represent cells which can, when transformed or transfected with the appropriate nucleotide coding sequences, express an antibody molecule of the disclosure in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

The host cell line used for protein expression is often of mammalian origin; those skilled in the art are credited with ability to determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3×63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used.

For long-term, high-yield production of recombinant proteins, stable expression is preferred. For example, cell lines which stably express the antibody molecule can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which stably express the antibody molecule.

A number of selection systems can be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 1980) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 *Clinical Pharmacy* 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); *TIB TECH* 11(5):155-215 (May, 1993); and hygro, which confers resistance to hygromycin (Santerre et al., *Gene* 30:147 (1984). Methods commonly known in the art of recombinant DNA technology which can be used are described in Ausubel et al. (eds.), *Current Protocols in Molecular Biology*, John Wiley & Sons, N Y (1993); Kriegler, *Gene Transfer and Expression*, A Laboratory Manual, Stockton Press, N Y (1990); and in Chapters 12 and 13, Dracopoli et al. (eds), *Current Protocols in Human Genetics*, John Wiley & Sons, N Y (1994); Colberre-Garapin et al., *J. Mol. Biol.* 150:1(1981), which are incorporated by reference herein in their entireties.

The expression levels of an antibody molecule can be increased by vector amplification (for a review, see Bebbington and Hentschel, *The use of vectors based on gene amplification for the expression of cloned genes in mammalian cells in DNA cloning*, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

In vitro production allows scale-up to give large amounts of the desired polypeptides.

Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Constructs encoding anti-Siglec-15 antibodies or fragments, variants or derivatives thereof, as disclosed herein can also be expressed non-mammalian cells such as bacteria or yeast or plant cells. Bacteria which readily take up nucleic acids include members of the enterobacteriaceae, such as strains of *Escherichia coli* or *Salmonella*; Bacillaceae, such as *Bacillus subtilis*; *Pneumococcus*; *Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies (WO02/096948A2).

In bacterial systems, a number of expression vectors can be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruther et al., *EMBO J.* 2:1791 (1983)), in which the antibody coding sequence can be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors can also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes can also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al., Nature 282:39 (1979); Kingsman et al., *Gene* 7:141 (1979); Tschemper et al., *Gene* 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, *Genetics* 85:12 (1977)). The presence of the trpl lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

Once the anti-Siglec-15 antibody or fragment, variant or derivative thereof, as disclosed herein has been recombinantly expressed, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

VI. Pharmaceutical Compositions Comprising Anti-Siglec-15 Antibodies or Antigen-Binding Fragments Thereof The pharmaceutical compositions used in this disclosure comprise pharmaceutically acceptable carriers well known to those of ordinary skill in the art. Preparations for parenteral administration include sterile aqueous or non-aqueous solutions, suspensions, and emulsions. Certain pharmaceutical compositions as disclosed herein can be orally administered in an acceptable dosage form including, e.g., capsules, tablets, aqueous suspensions or solutions. Certain pharmaceutical compositions also can be administered by nasal aerosol or inhalation. Preservatives and other additives can also be present such as for example, antimicrobials, antioxidants, chelating agents, and inert gases and the like. Suitable formulations for use in the therapeutic methods disclosed herein are described in Remington's Pharmaceutical Sciences, Mack Publishing Co., 16th ed. (1980).

The amount of an anti-Siglec-15 antibody or immunoconjugate, that can be combined with the carrier materials to produce a single dosage form will vary depending upon the host treated and the particular mode of administration. Dosage regimens also can be adjusted to provide the optimum desired response. The compositions can also comprise the Siglec-15 immunoconjugates, antibodies or fragments, variants or derivatives thereof dispersed in a biocompatible carrier material that functions as a suitable delivery or support system for the compounds.

VII. Treatment Methods Using Therapeutic Immunoconjugates, Antibodies or Antigen-Binding Fragments Thereof Methods of preparing and administering a Siglec-15 an immunoconjugate, antibody or fragment, variant or derivative thereof, as disclosed herein to a subject in need thereof are well known to or are readily determined by those skilled in the art.

Siglec-15 immunoconjugates, antibodies or antigen-binding fragments thereof of the invention are useful for the treatment of a leukemia, such as AML. In certain embodiments, the Siglec-15 immunoconjugates, antibodies or antigen-binding fragments thereof advantageously reduce side effects associated with conventional leukemic therapies.

Leukemia's are cancers that originate in the bone marrow, where the malignant cells are white blood cells (leukocytes). Acute myelogenous leukemia (also called acute myelocytic leukemia, acute myeloblastic leukemia, acute granulocytic leukemia, and acute nonlymphocytic leukemia) is a malignancy that arises in either granulocytes or monocytes. AML is characterized by the uncontrolled, exaggerated growth and accumulation of cells called leukemic blasts, which fail to function as normal blood cells, and the blockade of the production of normal marrow cells, leading to a deficiency of red cells (anemia), and platelets (thrombocytopenia) and normal white cells (especially neutrophils, i.e., neutropenia) in the blood.

CD33-targeted therapies, such as GO, produce significant side effects including an infusion syndrome when administered to AML patients. Thus, the ability to target Siglec-15 for therapy provides an alternative to CD33-based treatments. Moreover, since leukemic blasts are both CD33+ and CD33−, anti-Siglec-15 antibodies or antigen-binding fragments thereof provide an additional treatment option for AML. This is important for several reasons. Improved cell killing can increase the percentage of complete remissions, increase remission time, and decrease the likelihood of relapse. Secondly, improved cell killing can decrease the total requirement for toxin therapy, resulting in decreased nonspecific cell killing and side effects. Thirdly, for those AML patients who have relatively low expression of CD33, either in the natural state or due to outgrowth of CD33-cells after undergoing CD33 therapy, Siglec-15 antibodies or antigen-binding fragments thereof are valuable alternative or combination therapeutics.

Moreover, since surface expression of Siglec-15 is low on peripheral blood leukocytes in normal control donors and high on blasts from AML patient, the side effects from administration of Siglec-15 immunoconjugates, antibodies or antigen-binding fragments thereof will be reduced compared to conventional leukemic therapies.

All subtypes of AML are suitable for treatment with an Siglec-15 antibody or antigen-binding fragment thereof. The subtypes of AML are classified based on the stage of development myeloblasts have reached at the time of diagnosis. The categories and subsets allow the physician to decide what treatment works best for the cell type and how quickly the disease may develop. The subsets are: M0, myeloblastic, on special analysis; M1, Myeloblastic, without maturation; M2, Myeloblastic, with maturation; M3, Promyelocytic; M4, Myelomonocytic; M5, Monocytic; M6, Erythroleukemia; and M7, Megakaryocytic. A Siglec-15 antibody or antigen-binding fragment thereof can be administered with a secondary agent that is particularly suited to the subtype of AML. For example, acute promyelocytic leukemia (APL) and acute monocytic leukemia are subtypes of AML that need different treatment than other subtypes of AML. A second agent for treatment of APL can include all-trans retinoic acid (ATRA) or an antimetabolite, such as cytarabine. A second agent for treatment of acute monocytic leukemia can include a deoxyadenosine analog, such as 2-chloro-2'-deoxyadenosine (2-CDA).

Risk factors of AML include the presence of certain genetic disorders, such as Down syndrome, Fanconi anemia, Shwachman-Diamond syndrome and others. A patient having AML and a genetic disorder can be administered a Siglec-15 antibody or antigen-binding fragment thereof and a second agent to treat a symptom of the genetic disorder. For example, a patient with AML and Fanconi anemia can be administered a Siglec-15 antibody or antigen-binding fragment thereof and an antibiotic.

Other risk factors for AML include chemotherapy or radiotherapy for treatment of a different cancer, tobacco smoke, and exposure to large amounts of benzene.

Siglec-15 immunoconjugates, antibodies or antigen-binding fragments thereof can be administered to a human or other animal in accordance with the aforementioned methods of treatment in an amount sufficient to produce a therapeutic effect. With respect to AML, therapy can be deemed to be effective if there is a statistically significant difference in the rate or proportion of malignant cells in the blood stream or bone marrow. Therapy is deemed to be effective, for example, when remission is achieved, which is when there are no signs of malignant cells.

Efficacy of administering a first agent and, optionally, a second agent, can also be evaluated based on, for example, the decrease of number of malignant cells found in the blood stream, a decrease in frequency or severity of bacterial or viral infection, increased rate of wound healing, and the general feeling of the patient, including increased energy level and decreased soreness in bones and joints.

The route of administration of the anti-Siglec-15 immunoconjugate, antibody or fragment, variant or derivative thereof, can be, for example, oral, parenteral, by inhalation or topical. The term parenteral as used herein includes, e.g., intravenous, intraarterial, intraperitoneal, intramuscular, or subcutaneous administration. A suitable form for administration would be a solution for injection, in particular for intravenous or intraarterial injection or drip.

Anti-Siglec-15 immunoconjugates, antibodies or antigen-binding fragments thereof can be administered multiple occasions at various frequencies depending on various factors known to those of skill in the art. Alternatively, anti-Siglec-15 immunoconjugates, antibodies or antigen-binding fragments thereof can be administered as a sustained release formulation, in which case less frequent administration is required. Dosage and frequency vary depending on the half-life of the immunoconjugate, antibody, or antigen-binding fragment in the patient.

\* \* \*

The practice of the disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), *DNA Cloning*, D. N. Glover ed., Volumes I and 11 (1985); *Oligonucleotide Synthesis*, M. J. Gait ed., (1984); Mullis et al. U.S. Pat. No. 4,683,195; *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, Alan R. Liss, Inc., (1987); *Immobilized Cells And Enzymes*, IRL Press, (1986); B. Perbal, *A Practical Guide To Molecular Cloning* (1984); the treatise, *Methods In Enzymology*, Academic Press, Inc., N.Y.; *Gene Transfer Vectors For Mammalian Cells*, J. H. Miller and M. P. Calos eds., Cold Spring Harbor Laboratory (1987); *Methods In Enzymology*, Vols. 154 and 155 (Wu et al. eds.); *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds., (1986); *Manipulating the Mouse Embryo*, Cold Spring Harbor Laboratory Press, Cold Spring Harbor, N.Y., (1986); and in Ausubel et al., *Current Protocols in Molecular Biology*, John Wiley and Sons, Baltimore, Md. (1989).

General principles of antibody engineering are set forth in *Antibody Engineering*, 2nd edition, C. A. K. Borrebaeck, Ed., Oxford Univ. Press (1995). General principles of protein engineering are set forth in *Protein Engineering, A Practical Approach*, Rickwood, D., et al., Eds., IRL Press at Oxford Univ. Press, Oxford, Eng. (1995). General principles of antibodies and antibody-hapten binding are set forth in: Nisonoff, A., *Molecular Immunology*, 2nd ed., Sinauer Associates, Sunderland, Mass. (1984); and Steward, M. W., *Antibodies, Their Structure and Function*, Chapman and Hall, New York, N.Y. (1984). Additionally, standard methods in immunology known in the art and not specifically described are generally followed as in *Current Protocols in Immunology*, John Wiley & Sons, New York; Stites et al. (eds), *Basic and Clinical—Immunology* (8th ed.), Appleton & Lange, Norwalk, Conn. (1994) and Mishell and Shiigi (eds), *Selected Methods in Cellular Immunology*, W.H. Freeman and Co., New York (1980).

Standard reference works setting forth general principles of immunology include *Current Protocols in Immunology*, John Wiley & Sons, New York; Klein, J., Immunology: *The Science of Self-Nonself Discrimination*, John Wiley & Sons, New York (1982); Kennett, R., et al., eds., *Monoclonal Antibodies, Hybridoma: A New Dimension in Biological Analyses*, Plenum Press, New York (1980); Campbell, A., "Monoclonal Antibody Technology" in Burden, R., et al., eds., *Laboratory Techniques in Biochemistry and Molecular Biology*, Vol. 13, Elsevere, Amsterdam (1984), *Kuby Immunnology* $4^{th}$ ed. Ed. Richard A. Goldsby, Thomas J. Kindt and Barbara A. Osborne, H. Freemand & Co. (2000); Roitt, I., Brostoff, J. and Male D., *Immunology* $6^{th}$ ed. London: Mosby (2001); Abbas A., Abul, A. and Lichtman, A., *Cellular and Molecular Immunology* Ed. 5, Elsevier Health Sciences Division (2005); Kontermann and Dubel, *Antibody Engineering*, Springer Verlan (2001); Sambrook and Russell, *Molecular Cloning: A Laboratory Manual*. Cold Spring Harbor Press (2001); Lewin, *Genes VIII*, Prentice Hall (2003); Harlow and Lane, *Antibodies: A Laboratory Manual*, Cold Spring Harbor Press (1988); Dieffenbach and Dveksler, *PCR Primer* Cold Spring Harbor Press (2003).

EXAMPLES

Example 1

Multiple Splicing and Transcript Induction of Siglec-15 in Leukemic Cell Lines

Four human Siglec-15 splice variants were identified by RT-PCR using specific primers. Electrophoresis of RT-PCR products from DAMI (megakaryocytic cell line), HEL (erythroleukaemic cell line) and K562 (erythroleukaemic cell line) are shown in FIG. 1A with exon maps generated after sequencing (FIG. 1A—right panel). Four different splice variants of Siglec-15 were identified from RT-PCR of cDNA from leukemic cell lines. The largest transcript (2D) comprised all exons and was used in further experiments.

Siglec-15 transcript was also found in 6 of 7 different cell lines tested (FIG. 1B). Only YT (natural killer-like leukemic cell line) showed no Siglec-15 transcript. Phorbomeristyl acetate (PMA) or lipopolysaccharide (LPS) stimulations over 48 hours up-regulated expression of the transcripts. GAPDH RT-PCR is shown underneath each panel to control for equal loading (0.4 kb). 293T cells were used as a negative control.

RT-PCR was also performed to identify Siglec-15 full length transcript in 7 cell lines derived from leukemic patients (FIG. 1B). These cell lines were also stimulated with either LPS or PMA for 48 hours. Siglec-15 transcript expression was found in 6 of 7 cell lines and up-regulation following stimulation was observed in all cases apart from in the CHRF-288-11 cell line. The full length transcript was the only one to be upregulated consistently. In the HL60 cell line, while PMA induced upregulation of the full-length transcript, LPS stimulation resulted in complete loss of this transcript. These results show that Siglec-15 exists in multiple splice variants and the full length transcript is inducible by LPS and PMA in many leukemic cell lines.

Example 2

Siglec-15 Antibodies or Antigen-Binding Fragments Thereof

Phage display was employed to select reagents that specifically bind to Siglec-15. Single chain fragment variable (ScFv) binders to purified Flag-His tagged Siglec-15 were amplified using phage display technology and further selected on the surface of CHO cells stably expressing HA-tagged Siglec-15 cloned in a pDisplay construct. A9E8 and A4C9 were two ScFv binders from these two rounds that were converted to murine IgG1 format. Both bound Siglec-15 by FACS (FIG. 2A) and confocal microscopy (FIG. 2B) and A4C9, also bound in Western blots (FIG. 2D).

These two antibodies are unlikely to cross-react with other Siglecs because the similarity between Siglec-15 and other Siglecs is very low (identity less than 35%). To confirm specificity of A9E8 and A4C9 to Siglec-15, the ScFv versions of the two antibodies were compared for their binding to CHO cells stably transfected with either HA-tagged Siglec-15, Siglec-11, Siglec-16 or untransfected CHO cells. These two antibodies bound Siglec-15 strongly, while no binding was observed for Siglec-11 and -16 transfectants (FIG. 2C). U937 is a well characterized cell line that endogenously expresses many Siglecs on its cell surface, including CD33, Siglec-5 and Siglec-9 (Nguyen D H et al 2006). A9E8 did not bind to U937 cell surface (FIG. 5A) again consistent with no cross-reactivity with other Siglecs.

Example 3

Siglec-15 Expression Patterns

It has been previously shown by immunohistochemistry that endogenous Siglec-15 is mostly intracellular (Angata et al 2007). This finding was confirmed by FACS analysis of unfixed as well as fixed and permeabilized leukemic cell lines, although these lines differed in relative levels of surface and intracellular expression (FIG. 3). Low surface expression may be explained by the requirement of a membrane adaptor protein, such as DAP12 and DAP10 (Angata et al 2007). To test for the requirement of a membrane adaptor protein, Flag-tagged Siglec-15 was transiently transfected into HEK-293 cell lines stably transfected with different adaptor molecules: DAP12, DAP10 or FcRγ. HEK-293 cells were chosen because they lack endogenous expression of these adaptors. Surface Flag-Siglec-15 expression was detected using anti-Flag monoclonal antibody by FACS. Increase in surface Siglec-15 was most notable in presence of DAP10, but significant expression was also observed in the presence of DAP12 and FcRγ (FIG. 4). A parallel experiment using Siglec-16 showed more specific DAP12-dependent surface expression (FIG. 4). These results show that Siglec-15 is a prominently intracellular antigen under normal growth conditions but some may access the cell surface, in conjunction with an adaptor. The apparent promiscuity of Siglec-15's dependence of adaptors for surface expression sets it apart from other activating receptors, which bind to one adaptor more specifically.

The antibody A9E8 was used to examine Siglec-15 surface expression on leukemic cell lines. By FACS, Siglec-15 was identified on the cell surface of leukemic cell lines of the erythroid (K562 and HEL) and megakaryocytic (DAMI) lineages (FIG. 5A). Monocytic (U937 and SKM-1) and promonocytic (NOMO-1) leukemic cell lines showed no cell surface expression (FIG. 5A). Leukemic cell lines of lymphoid lineages were also tested. Only Daudi (B cell lymphoma) showed, relatively weak, surface expression (FIG. 5A). There was no expression on Jurkat T cell lymphoblastic leukemia (FIG. 5A).

Western blot analysis of selected cell lines by monoclonal antibody A4C9 showed a similar pattern of expression to a rabbit anti-serum, 1A, specific to the cytoplasmic tail of Siglec-15, which bound transfectant Flag-tagged Siglec-15 in 293T cells (FIGS. 5B and 5C). The western blots revealed significant Siglec-15 protein expression in Jurkat cells (band indicated by single arrows) and weaker expression in K562 and HEL cell lines (FIG. 5C).

Example 4

Siglec-15 Surface Expression on Peripheral Blood Leukocytes from Healthy Donors

Healthy donor peripheral blood cells were used for studying Siglec-15 expression. Siglec-15 was absent on the surface of most mature leukocytes tested: T cells (CD3+), B cells (CD19+) and NK cells (CD56+) but rare populations (<1%) of monocytes (CD14+) showed Siglec-15 surface expression (FIG. 6A). This pattern of expression was similar in six healthy donors tested.

Siglec-15 was previously reported to be intracellular in macrophages and dendritic cells by immunohistochemistry. FACS analysis showed very weak levels of Siglec-15 surface expression on 7% of cultured macrophages derived from peripheral blood monocytes (FIG. 6B). The Siglec-15 staining was more prominent on cells of low forward scatter, probably corresponding to a less mature subpopulation of macrophages. The surface staining on macrophages was lost following 24 hours of LPS treatment (FIG. 6B). Dendritic cells showed extremely low Siglec-15 surface expression on ~4% of the total population before LPS stimulation (FIG. 6B). This expression was also lost following 24 hours of LPS stimulation (FIG. 6B). These results show that in healthy donors, Siglec-15 is low or absent on the cell surface of most blood circulating leukocytes, as it was on macrophages and dendritic cells derived from monocytes.

Example 5

Siglec-15 Surface Expression on Circulating AML Blasts

In contrast to healthy donors, significantly higher Siglec-15 surface expression was found on blasts in 8 out of 10 AML patients tested (FIG. 7A-D). The average size of blast subpopulations positive for Siglec-15 was 20%, compared to ~2% for circulating peripheral blood leukocytes from healthy donors (FIG. 7E). Four examples representative of the group of AML donors studied are summarized in FIG. 7. Patients A (FIG. 7A), B (FIG. 7B) and C (FIG. 7C) consistently showed co-expression of Siglec-15 with CD14.

CD33 is expressed on 90% of AML myeloblasts. In one case, patient C (FIG. 7C), who was CD33-negative, a high level of Siglec-15 was expressed on 20% of blasts. In another case, patient D showed a low percentage of CD33+ blasts (7%) but a higher proportion of Siglec-15+ blasts (15%) (data not shown). HLA-DR was not consistently co-expressed with Siglec-15, except in certain patients, such as A. Patient D expressed more Siglec-15 on larger blasts, as defined by greater forward scatter. These data indicate that Siglec-15 exhibits significantly higher expression on circulating white cells from AML patients than from healthy donors.

Example 6

A9E8 Induces an Extremely Rapid Rate of Endocytosis of Surface Siglec-15

A fast rate of Siglec-15 endocytosis would be advantageous particularly if a toxin-conjugated antibody were to be used to target Siglec-15 positive AML blasts. Rapid endocytosis of Siglec-15 is expected from its cytoplasmic tail sequence, which encodes an ITSM motif of sequence SNYENL and therefore conforms to the classical endocytosis YxxΦ motif, where X is any amino acid and Φ is a hydrophobic residue. The YxxΦ motif directs clathrin-dependent endocytosis of membrane proteins (Collawn et al 1990) by binding to the AP2 clathrin adaptor complex (Aguilar et al 2001; Boehm and Bonifacino, 2001). To investigate the rate of endogenous Siglec-15 endocytosis in vitro, the K562 cell line was chosen because it shows significant surface expression. The A9E8 antibody was bound to K562 on ice and cells were resuspended in media pre-warmed to 37° C. Warmed cells were immediately incubated for various times at 37° C., before cooling with 5 ml of ice-cold FACS buffer. Secondary antibody was used to detect remaining surface antibody and the half-life of endocytosis was measured at 174 seconds. To control for natural dissociation of the A9E8 antibody from Siglec-15, a pDisplay construct encoding only the extracellular domains of Siglec-15 was subjected to the same assay. Lacking the natural transmembrane and cytoplasmic tail of Siglec-15, this construct exhibited no apparent surface endocytosis during the first fifteen minutes of incubation at 37° C. This result shows that disappearance of surface A9E8 staining on K562 cells is most likely due to endocytosis.

* * *

The disclosure is not to be limited in scope by the specific embodiments described which are intended as single illustrations of individual aspects of the disclosure, and any compositions or methods which are functionally equivalent are within the scope of this disclosure. Indeed, various modifications of the disclosure in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. An isolated polynucleotide comprising a nucleic acid encoding an antibody or antigen-binding fragment thereof that specifically binds to Siglec-15, wherein the antibody or antigen-binding fragment thereof comprises SEQ ID NO:3, SEQ ID NO:4, SEQ ID NO:5, SEQ ID NO:6, SEQ ID NO:7 and SEQ ID NO:8.

2. The polynucleotide according to claim 1, wherein said antibody or antigen-binding fragment thereof induces endocytosis of Siglec-15 at a rate where the half-life of endogenous surface Siglec-15 on human myelogenous leukemia K562 cells is less than about 5 minutes, less than about 4 minutes, or less than about 3 minutes.

3. The polynucleotide according to claim 1, wherein said antibody or antigen-binding fragment thereof is at least 95% identical to SEQ ID NO:1 and at least 95% identical to SEQ ID NO:2.

4. The polynucleotide according to claim 1, wherein said antibody or antigen-binding fragment thereof is humanized, chimeric, fully human, a Fab fragment, a Fab' fragment, a F(ab)2 fragment, or a single chain Fv (scFv) fragment.

5. The polynucleotide according to claim 1, wherein said antibody or antigen-binding fragment thereof comprises SEQ ID NO: 1 and SEQ ID NO:2.

6. The polynucleotide according to claim 1 comprising a nucleotide sequence at least 85%, 90%, or 95% identical to SEQ ID NO:9 and/or at least 85%, 90%, or 95% identical to SEQ ID NO:10.

7. The polynucleotide according to claim 1, wherein the nucleic acid is operably linked to a control sequence.

8. A vector comprising the polynucleotide of claim 1.

9. An isolated polynucleotide comprising SEQ ID NO:9 and/or SEQ ID NO:10.

10. The polynucleotide according to claim 9, wherein the nucleic acid is operably linked to a control sequence.

11. A vector comprising the polynucleotide of claim 9.

* * * * *